(12) United States Patent
Dror et al.

(10) Patent No.: US 12,099,629 B2
(45) Date of Patent: Sep. 24, 2024

(54) ASSIGNING CONFIDENCE TO DATA DE-IDENTIFICATION

(71) Applicant: LYNX MD LTD, Tel Aviv (IL)

(72) Inventors: Omer Dror, Sunnyvale, CA (US); Ofir Farchy, Modiin (IL)

(73) Assignee: LYNX MD LTD, Tel Aviv (IL)

( * ) Notice: Subject to any disclaimer, the term of this patent is extended or adjusted under 35 U.S.C. 154(b) by 309 days.

(21) Appl. No.: 17/676,141

(22) Filed: Feb. 19, 2022

(65) Prior Publication Data

US 2022/0179994 A1 Jun. 9, 2022

Related U.S. Application Data

(60) Provisional application No. 63/151,751, filed on Feb. 21, 2021, provisional application No. 63/151,745, filed on Feb. 21, 2021, provisional application No. 63/151,748, filed on Feb. 21, 2021.

(51) Int. Cl.
*G06F 21/62* (2013.01)
*G16H 10/60* (2018.01)
*G16H 40/20* (2018.01)
*G16H 40/63* (2018.01)
*G16H 40/67* (2018.01)

(52) U.S. Cl.
CPC ...... *G06F 21/6245* (2013.01); *G06F 21/6209* (2013.01); *G06F 21/6254* (2013.01); *G06F 21/6272* (2013.01); *G16H 10/60* (2018.01); *G16H 40/20* (2018.01); *G16H 40/63* (2018.01); *G16H 40/67* (2018.01)

(58) Field of Classification Search
None
See application file for complete search history.

(56) References Cited

U.S. PATENT DOCUMENTS

| 2002/0194178 | A1* | 12/2002 | Gilmour | H04L 63/10 |
| | | | | 707/999.009 |
| 2015/0149208 | A1* | 5/2015 | Lynch | G16H 10/60 |
| | | | | 705/3 |
| 2016/0132697 | A1* | 5/2016 | Simske | G06F 21/6254 |
| | | | | 726/26 |
| 2017/0177907 | A1* | 6/2017 | Scaiano | G06F 21/6254 |
| 2018/0082020 | A1* | 3/2018 | Rajagopal | G06F 21/6254 |
| 2021/0240853 | A1* | 8/2021 | Carlson | G16H 10/20 |

* cited by examiner

*Primary Examiner* — Joseph P Hirl
*Assistant Examiner* — Hassan Saadoun
(74) *Attorney, Agent, or Firm* — The Roy Gross Law Firm, LLC; Roy Gross

(57) ABSTRACT

Systems, methods and non-transitory computer readable media for assigning confidence to data de-identification are provided. A data collection may be accessed to generate a de-identified copy of the data collection. A confidence level that the generated de-identified copy does not include identified information may be determined. In response to a first value of the confidence level, providing particular information based on the de-identified copy of the data collection to a first entity and to a second entity. In response to a second value of the confidence level, providing the particular information to the first entity and forgoing providing the particular information to the second entity.

20 Claims, 12 Drawing Sheets

900

902 Accessing a data collection to generate a de-identified copy of the data collection 904 Determining a confidence level that the generated de-identified copy does not include identified information 906 In response to a first value of the confidence level, providing particular information based on the de-identified copy of the data collection to a first entity and to a second entity 908 In response to a second value of the confidence level, providing the particular information to the first entity and forgoing providing the particular information to the second entity

| 752 Patient Name | 754 Patient Phone Number | 756 Physician Name | 758 Appointment Time |
|---|---|---|---|
| Mary Smith | 555-#### | James Miller | Dec. 16, 10:50 |
| John Brown | 555-#### | Linda Jones | Dec. 16, 9:10 |

800

802 Receiving a first query, a second query and a third query associated with medical data

804 Accessing the medical data to determine a possible response to the first query, a possible response to the second query, and a possible response to the third query

806 Determining a first privacy loss level associated with the possible response to the first query, a second privacy loss level associated with the possible response to the second query, and a third privacy loss level associated with the possible response to the third query, wherein the first privacy loss level and the second privacy loss level are identical

808 Determining a first confidence level for the determination of the first privacy loss level, and a second confidence level for the determination of the second privacy loss level, wherein the second confidence level is lower than the first confidence level

810 In response to the first privacy loss level and the first confidence level, providing the possible response to the first query

812 In response to the third privacy loss level, avoiding providing the possible response to the third query

814 In response to the second privacy loss level and the second confidence level, involve a manual review in the determination of whether to provide or to avoid providing the possible response to the second query

| 822 Providing to a user information indicative of at least one aspect of the possible response to a particular query |

| 824 Receiving an input from the user |

| 826 Determining whether to provide or to avoid providing the possible response to the particular query based on the input received from the user. |

| 842 Receiving a fourth query associated with the medical data |

| 844 Accessing the medical data to determine a possible response to the fourth query |

| 846 Determining a fourth privacy loss level associated with the possible response to the fourth query, wherein the fourth privacy loss level is identical to the first privacy loss level and the second privacy loss level |

| 848 Determining a fourth confidence level for the determination of the fourth privacy loss level, wherein the fourth confidence level is between the second confidence level and the first confidence level |

| 850 Accessing users availability data |

| 852 In response to the fourth privacy loss level and the fourth confidence level, determining based on the users availability data whether to involve manual review in a determination of whether to provide the possible response to the fourth query |

| 902 Accessing a data collection to generate a de-identified copy of the data collection |

| 904 Determining a confidence level that the generated de-identified copy does not include identified information |

| 906 In response to a first value of the confidence level, providing particular information based on the de-identified copy of the data collection to a first entity and to a second entity |

| 908 In response to a second value of the confidence level, providing the particular information to the first entity and forgoing providing the particular information to the second entity |

| 922 Analyzing a first image included in the data collection but not included in the de identified copy to determine a visual characteristic |

| 924 Analyzing a second image included in the data collection and in the de-identified copy to determine a likelihood that the second image includes the visual characteristic |

| 926 Determining the confidence level that the generated de-identified copy does not include identified information based on the determined likelihood |

┌─────────────────────────────────────────────────────────┐
│ 902  Accessing a data collection to generate a de-identified copy of the data collection │
└─────────────────────────────────────────────────────────┘
                              ↓
┌─────────────────────────────────────────────────────────┐
│ 1004  Determining a first amount of residual identified information of a first type of residual identified information in the generated de-identified copy │
└─────────────────────────────────────────────────────────┘
                              ↓
┌─────────────────────────────────────────────────────────┐
│ 1006  Determining a second amount of residual identified information of a second type of residual identified information in the generated de-identified copy, the second type differs from the first type │
└─────────────────────────────────────────────────────────┘
                              ↓
┌─────────────────────────────────────────────────────────┐
│ 1008  Selecting a usage policy for the generated de-identified copy based on the first amount of residual identified information and the second amount of residual identified information in the generated de-identified copy │
└─────────────────────────────────────────────────────────┘
                              ↓
┌─────────────────────────────────────────────────────────┐
│ 1010  Implementing the selected usage policy │
└─────────────────────────────────────────────────────────┘

FIG. 10

ASSIGNING CONFIDENCE TO DATA DE-IDENTIFICATION

CROSS REFERENCES TO RELATED APPLICATIONS

This application claims the benefit of priority of U.S. Provisional Patent Application No. 63/151,745, filed on Feb. 21, 2021, U.S. Provisional Patent Application No. 63/151,748, filed on Feb. 21, 2021, and U.S. Provisional Patent Application No. 63/151,751, filed on Feb. 21, 2021.

The entire contents of all of the above-identified applications are herein incorporated by reference.

BACKGROUND

Technological Field

The disclosed embodiments generally relate to systems and methods for data de-identification. More particularly, the disclosed embodiments relate to systems and methods for assigning confidence to data de-identification.

Background Information

Numerous medical records are created, read and edited by vast number of medical care providers. Nowadays, some medical research requires access to large datasets of medical information. However, accessing medical data may prove challenging, partly due to regulatory and privacy requirements. Easing access to medical data may facilitate accelerated medical research.

Other data collections may include private information. Access to these data collection may be limited due to regulatory and privacy requirements. Easing access to such data collection may facilitate accelerated research and may mitigate other processes.

SUMMARY

Embodiments consistent with the present disclosure provide systems, methods, and devices for providing information based on private data, such as private medical data.

In some embodiments, systems, methods and non-transitory computer readable media for hybrid differential privacy are provided. In some examples, a first query, a second query and a third query associated with medical data may be received. The medical data may be accessed to determine a possible response to the first query, a possible response to the second query, and a possible response to the third query. A first privacy loss level associated with the possible response to the first query may be determined. A second privacy loss level associated with the possible response to the second query may be determined. A third privacy loss level associated with the possible response to the third query may be determined. The first privacy loss level and the second privacy loss level may be identical. A first confidence level may be determined for the determination of the first privacy loss level. A second confidence level may be determined for the determination of the second privacy loss level. The second confidence level may be lower than the first confidence level. In response to the first privacy loss level and the first confidence level, the possible response to the first query may be provided. In response to the third privacy loss level, providing the possible response to the third query may be avoided. In response to the second privacy loss level and the second confidence level: information indicative of at least one aspect of the possible response to the second query may be provided to a user, an input may be received from the user, and it may be determined whether to provide or to avoid providing the possible response to the second query based on the input received from the user.

In some embodiments, systems, methods and non-transitory computer readable media for assigning confidence to data de-identification are provided. In some examples, a data collection may be accessed to generate a de-identified copy of the data collection. A confidence level that the generated de-identified copy does not include identified information may be determined. In response to a first value of the confidence level, particular information may be provided based on the de-identified copy of the data collection to a first entity and to a second entity. In response to a second value of the confidence level, the particular information may be provided to the first entity, and providing the particular information to the second entity may be forwent.

In some embodiments, systems, methods and non-transitory computer readable media for estimating residual privacy loss after data de-identification are provided. In some examples, a data collection may be accessed to generate a de-identified copy of the data collection. A first amount of residual identified information of a first type of residual identified information in the generated de-identified copy may be determined. A second amount of residual identified information of a second type of residual identified information in the generated de-identified copy may be determined. The second type may differ from the first type. A usage policy for the generated de-identified copy may be selected based on the first amount of residual identified information and the second amount of residual identified information in the generated de-identified copy. The selected usage policy may be implemented.

Consistent with other disclosed embodiments, a non-transitory computer readable medium may store software programs, each software program comprising data and computer implementable instructions for carrying out any of the methods described herein. For example, when the software program is executed by at least one processing device, it may be configured to perform any of the methods described herein.

The foregoing general description and the following detailed description are exemplary and explanatory only and are not restrictive of the claims.

BRIEF DESCRIPTION OF THE DRAWINGS

FIG. 8A illustrates an example of a method for hybrid differential privacy.

FIG. 8B illustrates an example of a method for involving manual review in the determination of whether to provide or to avoid providing the possible response to a query.

FIG. 8C illustrates an example of a method for hybrid differential privacy.

FIG. 9A illustrates an example of a method for assigning confidence to data de-identification.

FIG. 9B illustrates an example of a method for assigning confidence to data de-identification.

FIG. 10 illustrates an example of a method for estimating residual privacy loss after data de-identification.

DESCRIPTION

Figure 1:
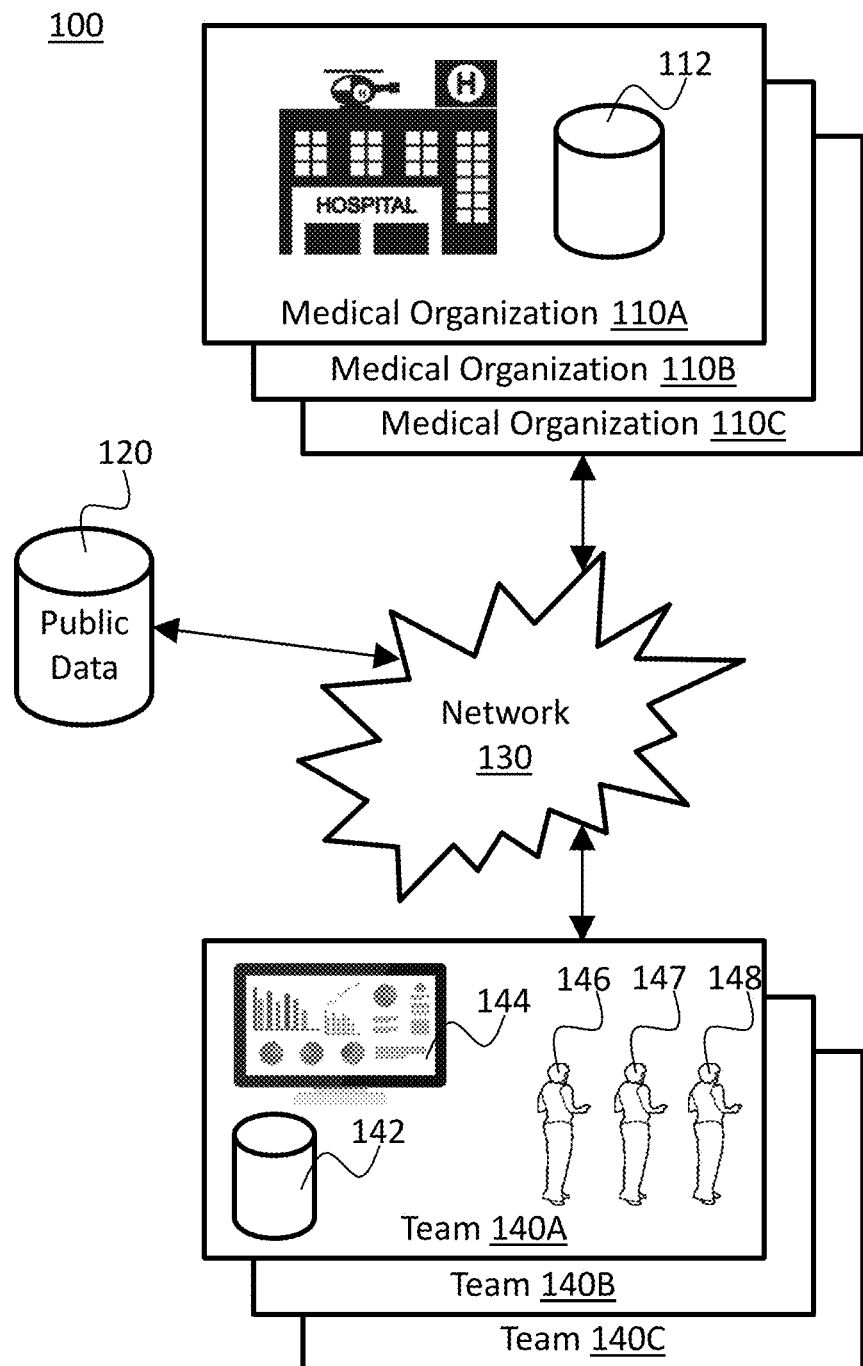
FIG. 1 is an illustration of an exemplary system for providing information based on medical data.

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects. The terms "computer", "processor", "controller", "processing unit", "computing device", and "processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

FIG. 1 is an illustration of an exemplary system 100 for providing information based on medical data. In some examples, system 100 may include one or more medical organizations 110 (in this example, medical organizations 110A, 110B and 110C). Some possible examples of such medical organizations 110 may include hospitals, medical clinics, medical labs, pharmacies, medical care providers 630 (described below), insurers 640 (described below), regulators 650 (described below), and so forth. Each one of the one or more medical organizations 110 may hold private medical data. In this example, medical organization 110A holds private medical data 112. Access to all or portions of private medical data 112 may be restricted, for example due to regulatory and privacy requirements, due to medical organization 110 procedures, and so forth. Some examples of such medical data 112 may include medical records 702 (described below), scheduling records 704 (described below), financial records 706 (described below), insurance records 708 (described below), research records 710 (described below), and so forth. In some examples, system 100 may include public data 120. Access to public data may be publically available to everyone. In some examples, system 100 may include one or more teams 140 (in this example, teams 140A, 140B and 140C). Some possible examples of such teams 140 may include research teams, research organizations, individual researchers, researchers 660 (described below), insurers 640 (described below), regulators 650 (described below), and so forth. In some example, each one of the one or more teams 140 may hold proprietary medical data. In this example, team 140A holds proprietary medical data 142. In some example, each one of the one or more teams 140 may use computerized data analysis devices. In this example, team 140A uses computerized data analysis device 144. Some possible implementations of computerized data analysis device 144 may include computing device 200 (described below), cloud platform 400 (described below), computational node 500 (described below), and so forth. In some example, each one of the one or more teams 140 may include one or more users. In this example, team 140A includes users 146, 147 and 148. Some possible examples of such users may include researchers 660 (described below), human data analysts, automated data analyst processes, and so forth. In some examples, data may be exchanged among elements of system 100, for example through communication network 130. Examples of communication network 130 may include the Internet, phone networks, cellular networks, satellite communication networks, private communication networks, virtual private networks (VPN), and so forth. Computerized devices (such as computing device 200, cloud platform 400, computational node 500, computerized data analysis device 144, storage devices, local storage, remote storage, network attached storage, etc.) may connect to communication network 130 directly, through local router, through wireless communication, through wired communication, and so forth.

In some examples, at least a portion of at least one of private medical data 112, public data 120 and proprietary medical data 142 may be stored in memory (such as memory 700, memory units 210, memory modules 410, etc.), in storage device (such as local storage, remote storage, network attached storage, etc.), and so forth. In some examples, at least a portion of at least one of private medical data 112, public data 120 and proprietary medical data 142 may be managed and/or controlled and/or maintained and/or collected and/or analyzed using local computing devices (such as computing device 200), local computerized servers, remote computerized servers, private and/or public cloud platforms (such as cloud platform 400), computational node (such as computational node 500), and so forth.

In some embodiments, a privacy firewall may be used to control access to data and enforce privacy rules. For example, a privacy firewall may be implemented using a computing device (such as computing device 200), may be implemented using a cloud platform (such as cloud platform 400), may be implemented as a software (for example in an operation system, as a software configured to be installed on a computing device, etc.), and so forth. In one example, a privacy firewall may be positioned on the connection between medical organization 110A and external network 130, for example to control all access to data in medical organization 110A from external entities and enforce privacy rules on access to data in medical organization 110A through network 130. In another example, a privacy firewall may be positioned on the connection between team 140A and external network 130, for example to control all access to external data from team 140A and enforce privacy rules on access of team 140A to data through network 130. In yet another example, a privacy firewall may be positioned within medical organization 110A to control access to private medical data 112, for example to control all access to private medical data 112, whether the access is coming from within medical organization 110A or from external sources and enforce privacy rules on access to private medical data 112. In an additional example, a privacy firewall may be installed on computerized data analysis device 144, for example to control all access to data from computerized data analysis device 144 and enforce privacy rules on access of computerized data analysis device 144 to data.

Figure 2A:
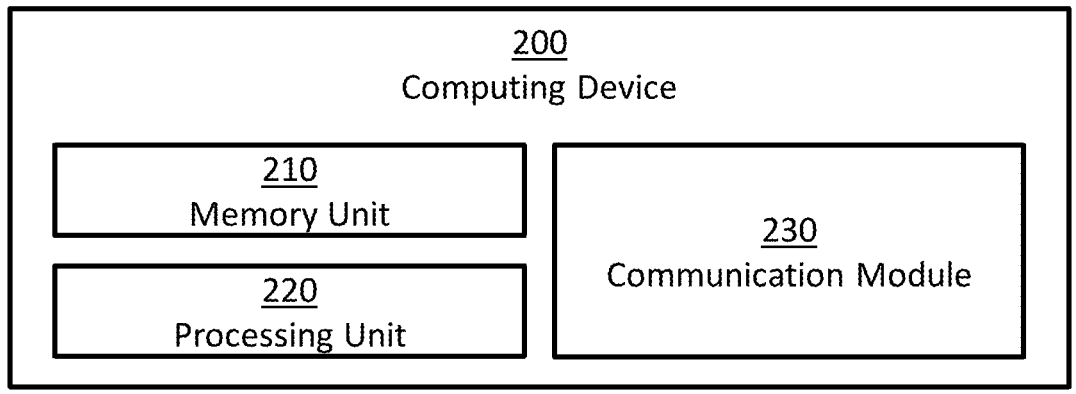
FIGS. 2A and 2B are block diagrams illustrating some possible implementations of a computing device.

FIG. 2A is a block diagram illustrating a possible implementation of computing device 200. In this example, computing device 200 may comprise: one or more memory units 210, one or more processing units 220, and one or more communication modules 230. In some implementations, computing device 200 may comprise additional components, while some components listed above may be excluded.

Figure 2B:
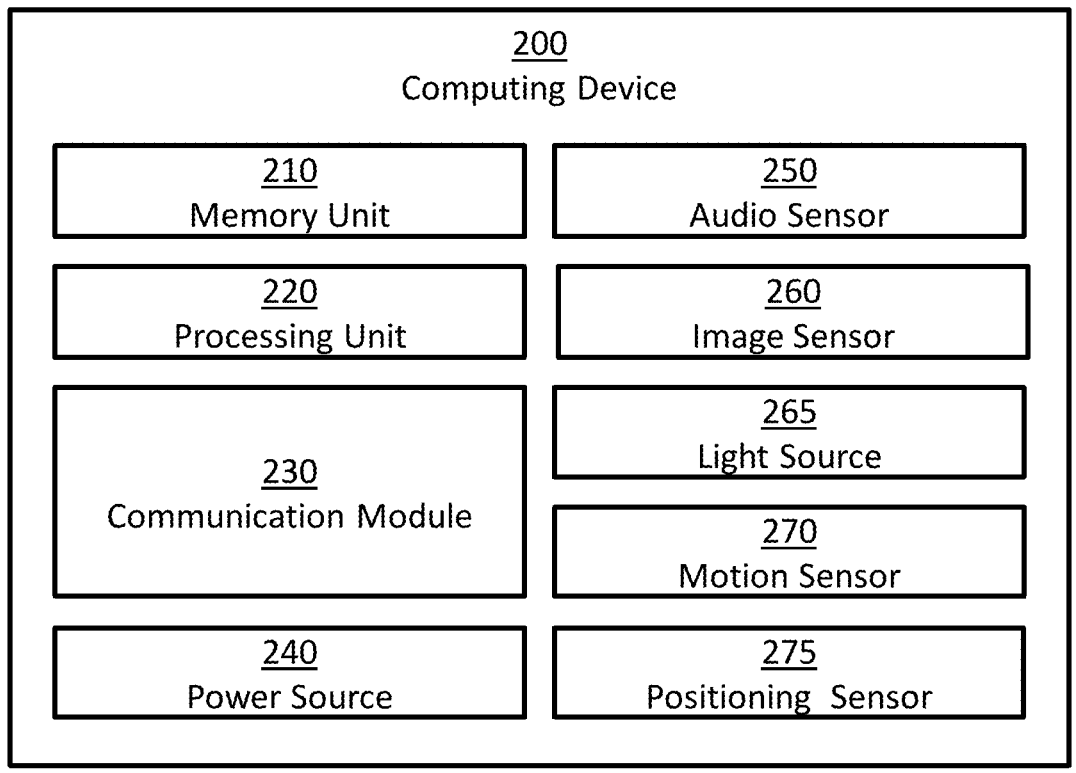

FIG. 2B is a block diagram illustrating a possible implementation of computing device 200. In this example, computing device 200 may comprise: one or more memory units 210, one or more processing units 220, one or more communication modules 230, one or more power sources 240, one or more audio sensors 250, one or more image sensors 260, one or more light sources 265, one or more motion sensors 270, and one or more positioning sensors 275. In some implementations, computing device 200 may comprise additional components, while some components listed above may be excluded. For example, in some implementations computing device 200 may also comprise at least one of the following: one or more barometers; one or more user input devices; one or more output devices; and so forth. In another example, in some implementations at least one of the following may be excluded from computing device 200: memory units 210, communication modules 230, power sources 240, audio sensors 250, image sensors 260, light sources 265, motion sensors 270, and positioning sensors 275.

In some embodiments, one or more power sources 240 may be configured to: power computing device 200, power cloud platform 400, and/or power computational node 500. Possible implementation examples of power sources 240 may include: one or more electric batteries; one or more capacitors; one or more connections to external power sources; one or more power convertors; any combination of the above; and so forth.

In some embodiments, the one or more processing units 220 may be configured to execute software programs. For example, processing units 220 may be configured to execute software programs stored on the memory units 210. In some cases, the executed software programs may store information in memory units 210. In some cases, the executed software programs may retrieve information from the memory units 210. Possible implementation examples of the processing units 220 may include: one or more single core processors, one or more multicore processors; one or more controllers; one or more application processors; one or more system on a chip processors; one or more central processing units; one or more graphical processing units; one or more neural processing units; any combination of the above; and so forth.

In some embodiments, the one or more communication modules 230 may be configured to receive and transmit information. For example, control signals may be transmitted and/or received through communication modules 230. In another example, information received though communication modules 230 may be stored in memory units 210. In an additional example, information retrieved from memory units 210 may be transmitted using communication modules 230. In another example, input data may be transmitted and/or received using communication modules 230. Examples of such input data may include: input data inputted by a user using user input devices; information captured using one or more sensors; and so forth. Examples of such sensors may include: audio sensors 250; image sensors 260; motion sensors 270; positioning sensors 275; chemical sensors; temperature sensors; barometers; and so forth.

In some embodiments, the one or more audio sensors 250 may be configured to capture audio by converting sounds to digital information. Some examples of audio sensors 250 may include: microphones, unidirectional microphones, bidirectional microphones, cardioid microphones, omnidirectional microphones, onboard microphones, wired microphones, wireless microphones, any combination of the above, and so forth. In some examples, the captured audio may be stored in memory units 210. In some additional examples, the captured audio may be transmitted using communication modules 230, for example to other computerized devices, such as cloud platform 400, computational node 500, and so forth. In some examples, processing units 220 may control the above processes. For example, processing units 220 may control at least one of: capturing of the audio; storing the captured audio; transmitting of the captured audio; and so forth. In some cases, the captured audio may be processed by processing units 220. For example, the captured audio may be compressed by processing units 220; possibly followed: by storing the compressed captured audio in memory units 210; by transmitted the compressed captured audio using communication modules 230; and so forth. In another example, the captured audio may be processed using speech recognition algorithms. In another example, the captured audio may be processed using speaker recognition algorithms.

In some embodiments, an image sensor 260 may include a device configured to capture images, a sequence of images, videos, and so forth. This includes sensors that convert optical input into images, where optical input can be visible light (like in a camera), radio waves, microwaves, terahertz waves, ultraviolet light, infrared light, x-rays, gamma rays, and/or any other light spectrum. This also includes both 2D and 3D sensors. Examples of image sensor technologies may include: CCD, CMOS, NMOS, and so forth. 3D sensors may be implemented using different technologies, including: stereo camera, active stereo camera, time of flight camera, structured light camera, radar, range image camera, and so forth. In some examples, the one or more image sensors 260 may be configured to capture visual information by converting light to: images; sequence of images; videos; 3D images; sequence of 3D images; 3D videos; and so forth. In some examples, the captured visual information may be stored in memory units 210. In some additional examples, the captured visual information may be transmitted using communication modules 230, for example to other computerized devices, such as cloud platform 400, computational node 500, and so forth. In some examples, processing units 220 may control the above processes. For example, processing units 220 may control at least one of: capturing of the visual information; storing the captured visual information; transmitting of the captured visual information; and so forth. In some cases, the captured visual information may be processed by processing units 220. For example, the captured visual information may be compressed by processing units 220; possibly followed: by storing the compressed captured visual information in memory units 210; by transmitted the compressed captured visual information using communication modules 230; and so forth. In another example, the captured visual information may be processed in order to: detect objects, detect events, detect action, detect face, detect people, recognize person, and so forth.

In some embodiments, the one or more light sources 265 may be configured to emit light, for example in order to enable better image capturing by image sensors 260. In some examples, the emission of light may be coordinated with the capturing operation of image sensors 260. In some examples, the emission of light may be continuous. In some examples, the emission of light may be performed at selected times. The emitted light may be visible light, infrared light, x-rays, gamma rays, and/or in any other light spectrum. In some examples, image sensors 260 may capture light emitted by light sources 265, for example in order to capture 3D images and/or 3D videos using active stereo method.

In some embodiments, the one or more motion sensors 270 may be configured to perform at least one of the following: detect motion of objects in the environment of computing device 200; measure the velocity of objects in the environment of computing device 200; measure the acceleration of objects in the environment of computing device 200; detect motion of computing device 200; measure the velocity of computing device 200; measure the acceleration of computing device 200; and so forth. In some implementations, the one or more motion sensors 270 may comprise one or more accelerometers configured to detect changes in proper acceleration and/or to measure proper acceleration of computing device 200. In some implementations, the one or more motion sensors 270 may comprise one or more gyroscopes configured to detect changes in the orientation of computing device 200 and/or to measure information related to the orientation of computing device 200. In some implementations, motion sensors 270 may be implemented using image sensors 260, for example by analyzing images captured by image sensors 260 to perform at least one of the following tasks: track objects in the environment of computing device 200; detect moving objects in the environment of computing device 200; measure the velocity of objects in the environment of computing device 200; measure the acceleration of objects in the environment of computing device 200; measure the velocity of computing device 200, for example by calculating the egomotion of image sensors 260; measure the acceleration of computing device 200, for example by calculating the egomotion of image sensors 260; and so forth. In some implementations, motion sensors 270 may be implemented using image sensors 260 and light sources 265, for example by implementing a LIDAR using image sensors 260 and light sources 265. In some implementations, motion sensors 270 may be implemented using one or more RADARs. In some examples, information captured using motion sensors 270: may be stored in memory units 210, may be processed by processing units 220, may be transmitted and/or received using communication modules 230, and so forth.

In some embodiments, the one or more positioning sensors 275 may be configured to obtain positioning information of computing device 200, to detect changes in the position of computing device 200, and/or to measure the position of computing device 200. In some examples, positioning sensors 275 may be implemented using one of the following technologies: Global Positioning System (GPS), GLObal NAvigation Satellite System (GLONASS), Galileo global navigation system, BeiDou navigation system, other Global Navigation Satellite Systems (GNSS), Indian Regional Navigation Satellite System (IRNSS), Local Positioning Systems (LPS), Real-Time Location Systems (RTLS), Indoor Positioning System (IPS), Wi-Fi based positioning systems, cellular triangulation, and so forth. In some examples, information captured using positioning sensors 275 may be stored in memory units 210, may be processed by processing units 220, may be transmitted and/or received using communication modules 230, and so forth.

In some embodiments, the one or more chemical sensors may be configured to perform at least one of the following: measure chemical properties in the environment of computing device 200; measure changes in the chemical properties in the environment of computing device 200; detect the present of chemicals in the environment of computing device 200; measure the concentration of chemicals in the environment of computing device 200. Examples of such chemical properties may include: pH level, toxicity, temperature, and so forth. Examples of such chemicals may include: electrolytes, particular enzymes, particular hormones, particular proteins, smoke, carbon dioxide, carbon monoxide, oxygen, ozone, hydrogen, hydrogen sulfide, and so forth. In some examples, information captured using chemical sensors may be stored in memory units 210, may be processed by processing units 220, may be transmitted and/or received using communication modules 230, and so forth.

In some embodiments, the one or more temperature sensors may be configured to detect changes in the temperature of the environment of computing device 200 and/or to measure the temperature of the environment of computing device 200. In some examples, information captured using temperature sensors may be stored in memory units 210, may be processed by processing units 220, may be transmitted and/or received using communication modules 230, and so forth.

In some embodiments, the one or more barometers may be configured to detect changes in the atmospheric pressure in the environment of computing device 200 and/or to measure the atmospheric pressure in the environment of computing device 200. In some examples, information captured using the barometers may be stored in memory units 210, may be processed by processing units 220, may be transmitted and/or received using communication modules 230, and so forth.

In some embodiments, the one or more user input devices may be configured to allow one or more users to input information. In some examples, user input devices may comprise at least one of the following: a keyboard, a mouse, a touch pad, a touch screen, a joystick, a microphone, an image sensor, and so forth. In some examples, the user input may be in the form of at least one of: text, sounds, speech, hand gestures, body gestures, tactile information, and so forth. In some examples, the user input may be stored in memory units 210, may be processed by processing units 220, may be transmitted and/or received using communication modules 230, and so forth.

In some embodiments, the one or more user output devices may be configured to provide output information to one or more users. In some examples, such output information may comprise of at least one of: notifications, feedbacks, reports, and so forth. In some examples, user output devices may comprise at least one of: one or more audio output devices; one or more textual output devices; one or more visual output devices; one or more tactile output devices; and so forth. In some examples, the one or more audio output devices may be configured to output audio to a user, for example through: a headset, a set of speakers, and so forth. In some examples, the one or more visual output devices may be configured to output visual information to a user, for example through: a display screen, an augmented reality display system, a printer, a LED indicator, and so forth. In some examples, the one or more tactile output devices may be configured to output tactile feedbacks to a user, for example through vibrations, through motions, by applying forces, and so forth. In some examples, the output may be provided: in real time, offline, automatically, upon request, and so forth. In some examples, the output information may be read from memory units 210, may be provided by a software executed by processing units 220, may be transmitted and/or received using communication modules 230, and so forth.

Figure 3:
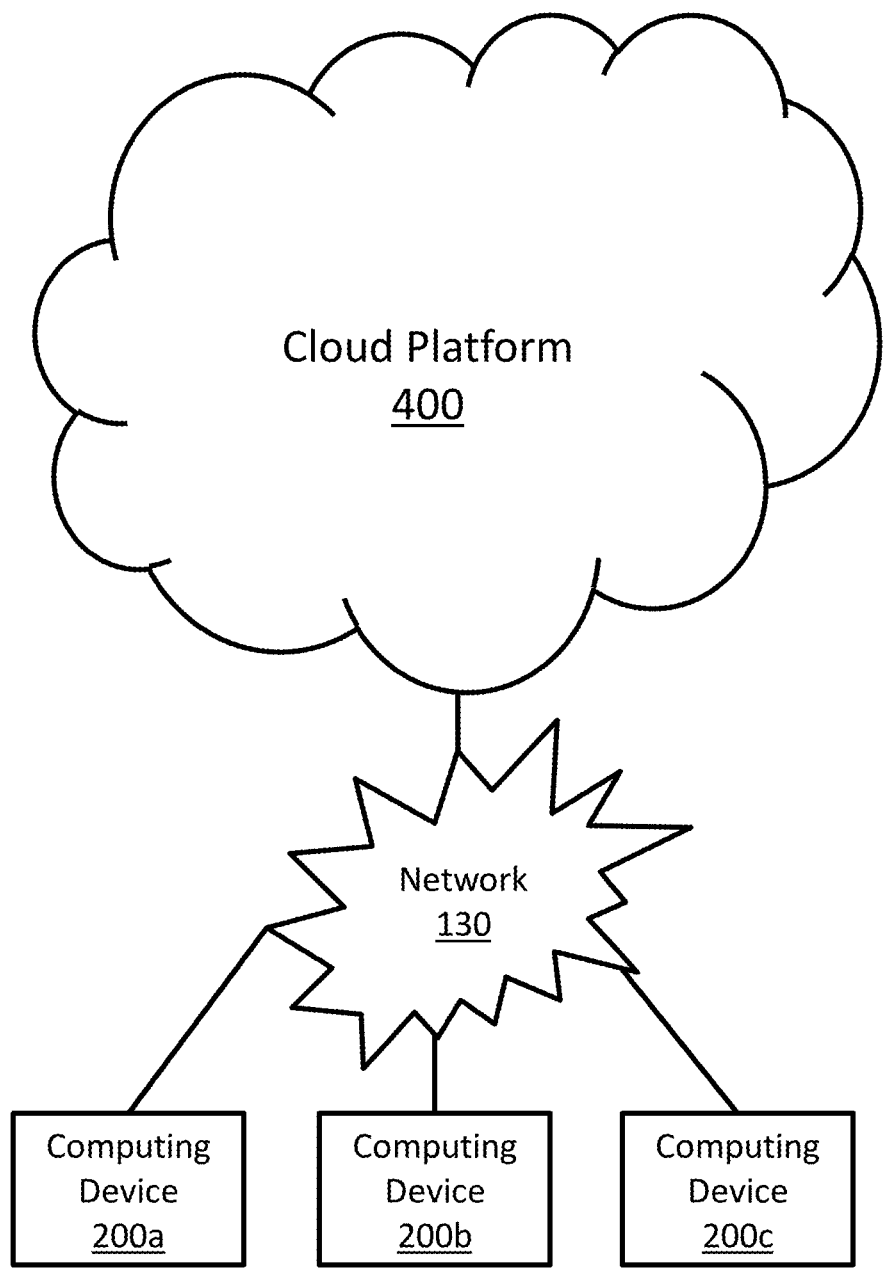
FIG. 3 is a block diagram illustrating a possible implementation of a communicating system.

FIG. 3 is a block diagram illustrating a possible implementation of a communicating system. In this example, computing devices 200a, 200b and 200c may communicate with cloud platform 400 and/or with each other through communication network 130. Possible implementations of computing devices 200a, 200b and 200c may include computing device 200 as described in FIGS. 2A and/or 2B. Some possible implementations of cloud platform 400 are described in FIGS. 4A, 4B and 5.

FIG. 3 illustrates a possible implementation of a communication system. In some embodiments, other communication systems that enable communication among computing devices and/or between a computing device (such as computing device 200) and a cloud platform (such as cloud platform 400) may be used.

Figure 4A:
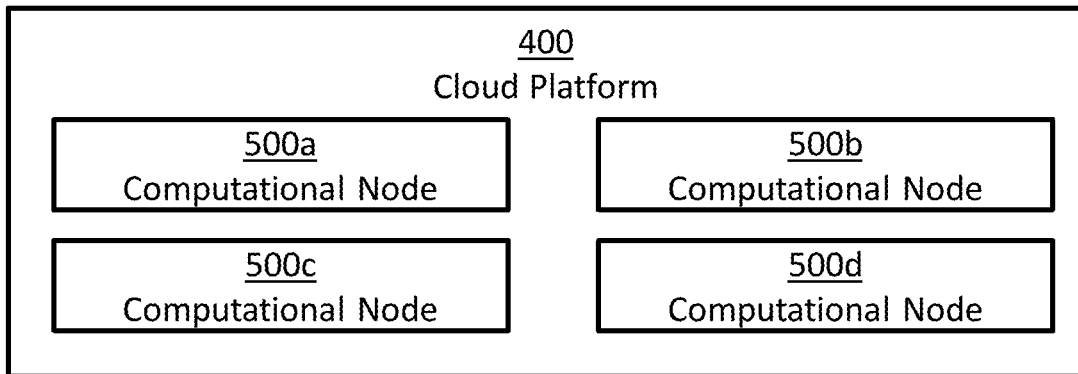
FIGS. 4A and 4B are block diagrams illustrating some possible implementations of a cloud platform.

FIG. 4A is a block diagram illustrating a possible implementation of cloud platform 400. In this example, cloud platform 400 may comprise computational node 500a, computational node 500b, computational node 500c and computational node 500d. In some examples, a possible implementation of computational nodes 500a, 500b, 500c and 500d may comprise computing device 200. In some examples, a possible implementation of computational nodes 500a, 500b, 500c and 500d may comprise computational node 500 as described in FIG. 5.

Figure 4B:
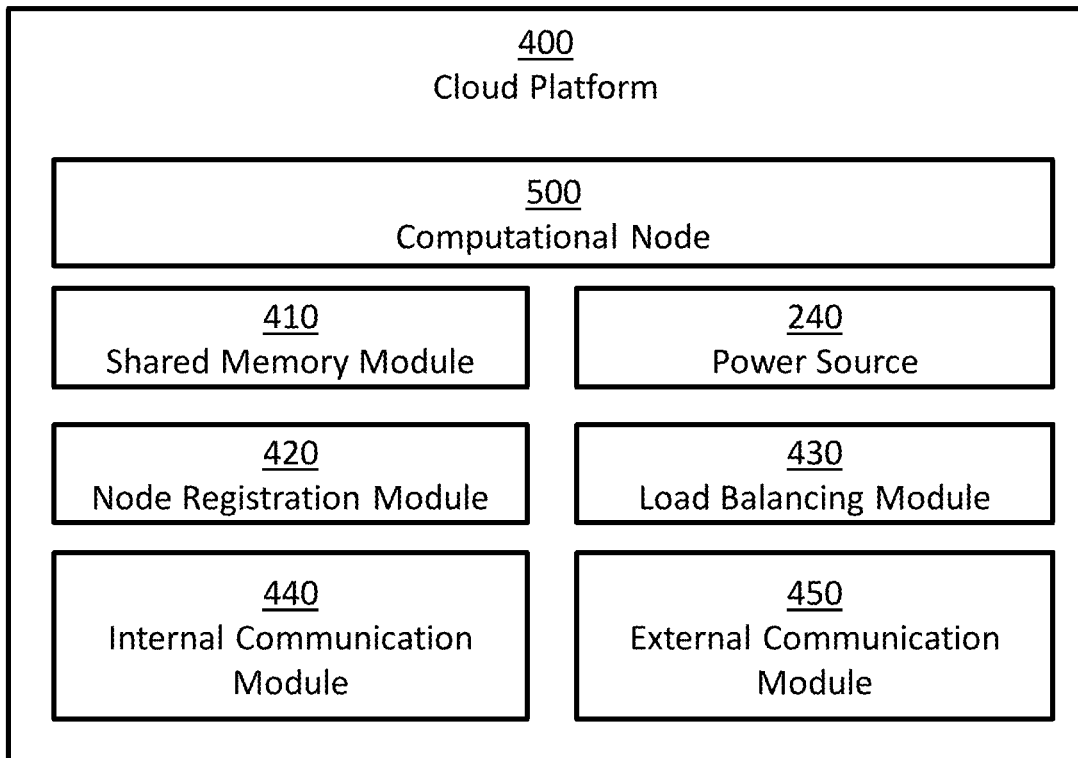

FIG. 4B is a block diagram illustrating a possible implementation of cloud platform 400. In this example, cloud platform 400 may comprise: one or more computational nodes 500, one or more shared memory modules 410, one or more power sources 240, one or more node registration modules 420, one or more load balancing modules 430, one or more internal communication modules 440, and one or more external communication modules 450. In some implementations, cloud platform 400 may comprise additional components, while some components listed above may be excluded. For example, in some implementations cloud platform 400 may also comprise at least one of the following: one or more user input devices; one or more output devices; and so forth. In another example, in some implementations at least one of the following may be excluded from cloud platform 400: shared memory modules 410, power sources 240, node registration modules 420, load balancing modules 430, internal communication modules 440, and external communication modules 450.

Figure 5:
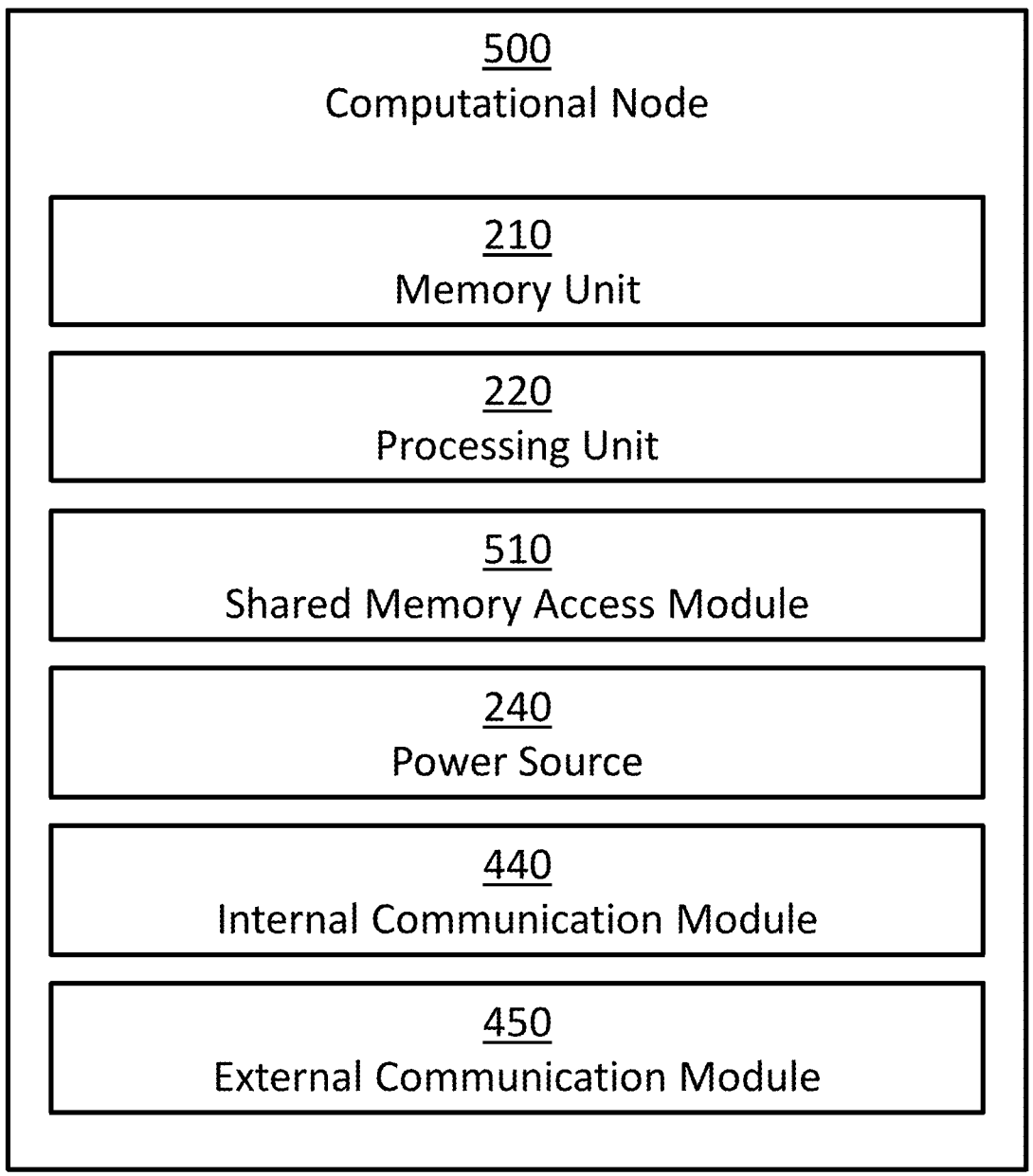
FIG. 5 is a block diagram illustrating a possible implementation of a computational node.

FIG. 5 is a block diagram illustrating a possible implementation of computational node 500. In this example, computational node 500 may comprise: one or more memory units 210, one or more processing units 220, one or more shared memory access modules 510, one or more power sources 240, one or more internal communication modules 440, and one or more external communication modules 450. In some implementations, computational node 500 may comprise additional components, while some components listed above may be excluded. For example, in some implementations computational node 500 may also comprise at least one of the following: one or more user input devices; one or more output devices; and so forth. In another example, in some implementations at least one of the following may be excluded from computational node 500: memory units 210, shared memory access modules 510, power sources 240, internal communication modules 440, and external communication modules 450.

In some embodiments, internal communication modules 440 and external communication modules 450 may be implemented as a combined communication module, such as communication modules 230. In some embodiments, one possible implementation of cloud platform 400 may comprise computing device 200. In some embodiments, one possible implementation of computational node 500 may comprise computing device 200. In some embodiments, one possible implementation of shared memory access modules 510 may comprise using internal communication modules 440 to send information to shared memory modules 410 and/or receive information from shared memory modules 410. In some embodiments, node registration modules 420 and load balancing modules 430 may be implemented as a combined module.

In some embodiments, the one or more shared memory modules 410 may be accessed by more than one computational node. Therefore, shared memory modules 410 may allow information sharing among two or more computational nodes 500. In some embodiments, the one or more shared memory access modules 510 may be configured to enable access of computational nodes 500 and/or the one or more processing units 220 of computational nodes 500 to shared memory modules 410. In some examples, computational nodes 500 and/or the one or more processing units 220 of computational nodes 500, may access shared memory modules 410, for example using shared memory access modules 510, in order to perform at least one of: executing software programs stored on shared memory modules 410, store information in shared memory modules 410, retrieve information from the shared memory modules 410.

In some embodiments, the one or more node registration modules 420 may be configured to track the availability of the computational nodes 500. In some examples, node registration modules 420 may be implemented as: a software program, such as a software program executed by one or more of the computational nodes 500; a hardware solution; a combined software and hardware solution; and so forth. In some implementations, node registration modules 420 may communicate with computational nodes 500, for example using internal communication modules 440. In some examples, computational nodes 500 may notify node registration modules 420 of their status, for example by sending messages: at computational node 500 startup; at computational node 500 shutdown; at constant intervals; at selected times; in response to queries received from node registration modules 420; and so forth. In some examples, node registration modules 420 may query about computational nodes 500 status, for example by sending messages: at node registration module 420 startup; at constant intervals; at selected times; and so forth.

In some embodiments, the one or more load balancing modules 430 may be configured to divide the work load among computational nodes 500. In some examples, load balancing modules 430 may be implemented as: a software program, such as a software program executed by one or more of the computational nodes 500; a hardware solution; a combined software and hardware solution; and so forth. In some implementations, load balancing modules 430 may interact with node registration modules 420 in order to obtain information regarding the availability of the computational nodes 500. In some implementations, load balancing modules 430 may communicate with computational nodes 500, for example using internal communication modules 440. In some examples, computational nodes 500 may notify load balancing modules 430 of their status, for example by sending messages: at computational node 500 startup; at computational node 500 shutdown; at constant intervals; at selected times; in response to queries received from load balancing modules 430; and so forth. In some examples, load balancing modules 430 may query about computational nodes 500 status, for example by sending messages: at load balancing module 430 startup; at constant intervals; at selected times; and so forth.

In some embodiments, the one or more internal communication modules 440 may be configured to receive information from one or more components of cloud platform 400, and/or to transmit information to one or more components of cloud platform 400. For example, control signals and/or synchronization signals may be sent and/or received through internal communication modules 440. In another example, input information for computer programs, output information of computer programs, and/or intermediate information of computer programs, may be sent and/or received through internal communication modules 440. In another example, information received though internal communication modules 440 may be stored in memory units 210, in shared memory units 410, and so forth. In an additional example, information retrieved from memory units 210 and/or shared memory units 410 may be transmitted using internal communication modules 440. In another example, input data may be transmitted and/or received using internal communication modules 440. Examples of such input data may include input data inputted by a user using user input devices.

In some embodiments, the one or more external communication modules 450 may be configured to receive and/or to transmit information. For example, control signals may be sent and/or received through external communication modules 450. In another example, information received though external communication modules 450 may be stored in memory units 210, in shared memory units 410, and so forth. In an additional example, information retrieved from memory units 210 and/or shared memory units 410 may be transmitted using external communication modules 450. In another example, input data may be transmitted and/or received using external communication modules 450. Examples of such input data may include: input data inputted by a user using user input devices; information captured from the environment of computing device 200 using one or more sensors; and so forth. Examples of such sensors may include: audio sensors 250; image sensors 260; motion sensors 270; positioning sensors 275; chemical sensors; temperature sensors; barometers; and so forth.

Figure 6:
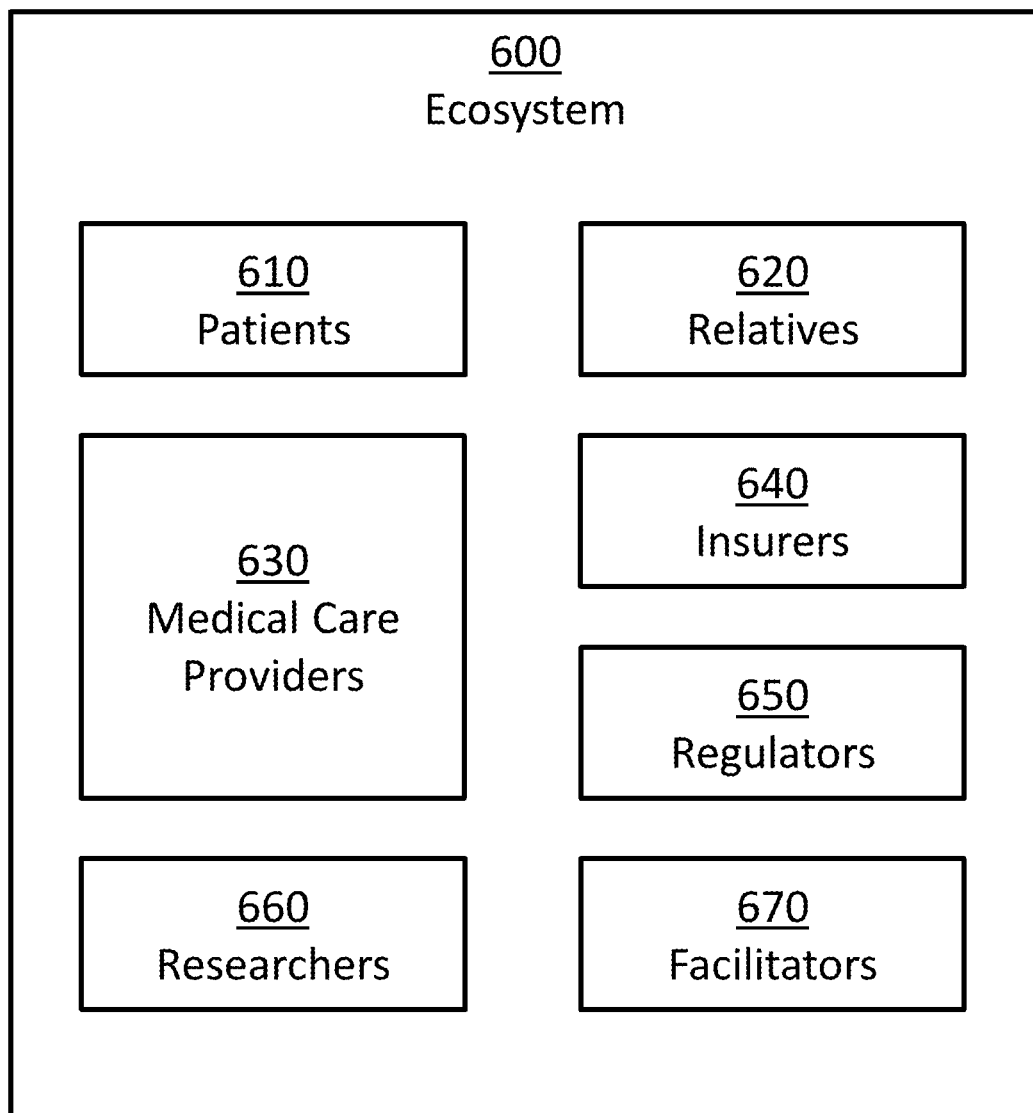
FIG. 6 is a block diagrams illustrating a possible ecosystem.

FIG. 6 is a block diagrams illustrating a possible ecosystem 600. In this example, the ecosystem may comprise one or more patients 610, one or more relatives 620, one or more medical care providers 630, one or more insurers 640, one or more regulators 650, one or more researchers 660, and one or more facilitators 670. In some embodiments, other ecosystems may exist. In some examples, ecosystem 600 may comprise one or more additional entities, while some of the entities listed above may be excluded from ecosystem 600. For example, patients 610 and/or relatives 620 and/or medical care providers 630 and/or insurers 640 and/or regulators 650 and/or researchers 660 and/or facilitators 670 may be excluded from ecosystem 600. For example, ecosystem 600 may further include financial institutes (such as banks, credit companies, etc.), legal firms, non-medical service providers, research institutes, and so forth.

In some embodiments, entities of ecosystem 600 (such as patients 610, relatives 620, medical care providers 630, insurers 640, regulators 650, researcher 660, facilitators 670, etc.) may use computerized devices (such as computing device 200, computational node 500, cloud platform 400, etc.) to perform part and/or all of their functions and/or duties. For example, the entities may use computerized devices to store and/or access and/or process data (some examples of such data may include medical records 702, scheduling records 704, financial records 706, insurance records 708, research records 710, indexes 712, identifiers 714, and/or permissions 716 described below), to communicate (for example over communication network 130), and so forth.

In some embodiments, patients 610 may comprise one or more individuals that received and/or are about to receive medical care.

In some embodiments, relatives 620 may comprise one or more individuals that have some bearing on the medical care of at least one patient 610. For example, relatives 620 may comprise one or more of a family member of patient 610, a friend of patient 610, a legal guardian of patient 610, a next of kin of patient 610, a non-medical care giver of patient 610, and so forth.

In some embodiments, medical care providers 630 may comprise one or more individual and/or one or more institutes that provides (in the past and/or present and/or future) medical care to patients 610. For example, medical care providers 630 may comprise one or more medical care professionals (such as medical doctors, nurses, therapists, stuff of medical care institutes, etc.), one or more medical care institutes (such as hospitals, clinics, labs, etc.), and so forth.

In some embodiments, insurers 640 may comprise one or more individuals and/or one or more institutes that cover medical expenses (such as medical expenses of at least some of patients 610 and/or medical care providers 630) and/or insures medical care providers 630 for malpractice costs. In some examples, insurers may include insurance firms and/or government agencies.

In some embodiments, regulators 650 may comprise official entities appointed to track and/or regulate the medical care provided to patents 610 and/or the medical care provided by medical care providers 630 and/or the medical care covered by insurers 640. For example, regulators 650 may comprise government agencies (such as the FDA, NIH, EMA, CFDA, PMDA, etc.), professional associations (such as the WMA, AMA, EMA, CMA, JMA, etc.), court appointed oversight, and so forth.

In some embodiments, researcher 660 may comprise research personals, research facilities, research institutes, research teams (such as teams 140A, 140B and 140C), and so forth. For example, researchers 660 may comprise a university, a drug development company, a research professor, and so forth.

In some embodiments, facilitators 670 may comprise individuals and/or entities that facilitate the communication among entities of ecosystem 600.

Figure 7A:
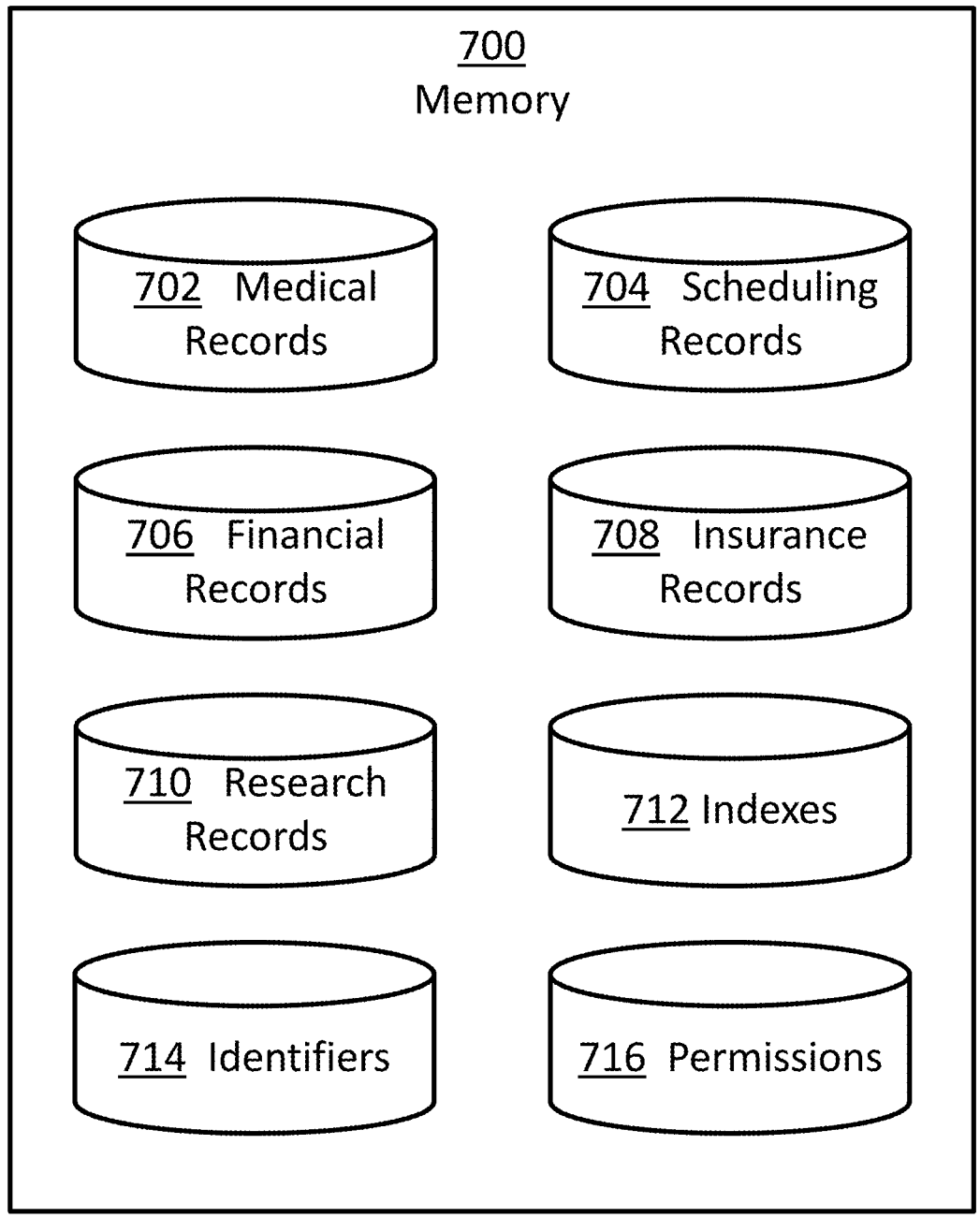
FIG. 7A illustrates an exemplary embodiment of a memory storing a plurality of modules.

FIG. 7A illustrates an exemplary embodiment of memory 700 storing a plurality of modules. In some examples, memory 700 may be separate from and/or integrated with memory units 210, separate from and/or integrated with memory units 410, and so forth. In some examples, memory 700 may be included in a single device, for example in computing device 200, in cloud platform 400, in computational node 500, and so forth. In some examples, memory 700 may be distributed across several devices. Memory 700 may store more or fewer modules than those shown in FIG. 7A. In this example, memory 700 may comprise: medical records 702, scheduling records 704, financial records 706, insurance records 708, research records 710, indexes 712, identifiers 714, and permissions 716.

In some embodiments, at least part of medical records 702 scheduling records 704, financial records 706, insurance records 708, research records 710, indexes 712, identifiers 714, and/or permissions 716 may be stored in a public database, in a public ledger, in a blockchain, in a computerized devices (such as computing device 200, cloud platform 400, computational node 500, etc.), in a storage devices (such as remote storage, network attached storage, etc.), and so forth. In some examples, medical records 702, scheduling records 704, financial records 706, insurance records 708, research records 710, indexes 712, identifiers 714, and/or permissions 716 may be stored in single database and/or blockchain and/or site and/or device, while in other examples medical records 702 may be distributed among a number of databases and/or blockchains and/or sites and/or devices. In some examples, medical records of a single entity (such as patient 610, relative 620, medical care provider 630, insurer 640, regulator 650, researcher 660, facilitator 670, etc.) may be stored in single database and/or blockchain and/or site and/or device, while in other examples the medical records of the entity may be distributed among a number of databases and/or blockchains and/or sites and/or devices.

In some embodiments, medical records 702 may comprise medical records of one or more patients 610, medical records created and/or used by one or more medical care providers 630, medical records associated with one or more patients and/or medical care providers insured by one or more insurers 640, medical records surveyed by one or more regulators 650, medical records studied by one or more researchers 660, and so forth. In some examples, medical records 702 may comprise medical information, such as information regarding medical conditions, medical care, medical treatment, EHR, genome data, and so forth.

In some embodiments, scheduling records 704 may comprise scheduling related information associated with patients 610 and/or relatives 620 and/or medical care providers 630 and/or insurers 640 and/or regulators 650 and/or researchers 660 and/or facilitators 670. The scheduling related information may relate to past and/or present and/or future events. For example, scheduling records 704 may comprise time and date information for an appointment, for a lab test, for a medical exam, for a medical checkup, for a reminder related to medical care, and so forth.

In some embodiments, financial records 706 may comprise financial information associated with patients 610 and/or relatives 620 and/or medical care providers 630 and/or insurers 640 and/or regulators 650 and/or researchers 660 and/or facilitators 670. The financial information may relate to past, present, and/or future budget, costs, bills, coverage obligations, and/or payments associated with medical care.

In some embodiments, insurance records 708 may comprise insurance information associated with patients 610 and/or relatives 620 and/or medical care providers 630 and/or insurers 640 and/or regulators 650 and/or researchers 660 and/or facilitators 670. The insurance information may include past, present and/or future coverage information, insurance claims, insurance payments, and so forth, associated with medical care.

In some embodiments, research records 710 may comprise research records associated with patients 610 and/or relatives 620 and/or medical care providers 630 and/or insurers 640 and/or regulators 650 and/or researchers 660 and/or facilitators 670. For example, research records 710 may comprise research records compiled and/or studied by a researcher 660. For example, research records 710 may comprise research records pertaining to one or more medical researches.

In some embodiments, indexes 712 may comprise one or more partial and/or complete indexes. In some examples, an index may link an identifier of a record (such as medical record 702 scheduling record 704, financial record 706, insurance record 708, research record 710, index 712, identifiers 714, permission 716, etc.) to entities (such as patients 610, relatives 620, medical care providers 630, insurers 640, regulators 650, researchers 660, facilitators 670, and so forth). For example, an index may link an identifier of a record to the entity created the record, to entities that accessed and/or edited the record, to entities that has permission to access and/or edit the record, and so forth.

In some examples, an index may link an identifier of an entity (such as patient 610, relative 620, medical care provider 630, insurer 640, regulator 650, researcher 660, facilitator 670, etc.) to records (such as medical records 702 scheduling records 704, financial records 706, insurance records 708, research records 710, indexes 712, identifiers 714, permissions 716, etc.) associated with the entity, to records that the entity has permissions to access and/or edit, to records accessed and/or edited by the entity, and so forth.

In some examples, an index may link an identifier of an entity (such as patient 610, relative 620, medical care provider 630, insurer 640, regulator 650, researcher 660, facilitator 670, etc.) to computerized devices (such as computing device 200, computational node 500, cloud platform 400, etc.) and/or to storage devices (such as remote storage, network attached storage, etc.) and/or to blockchains and/or to databases containing information and/or at least part of the records (such as medical records 702 scheduling records 704, financial records 706, insurance records 708, research records 710, indexes 712, identifiers 714, permissions 716, etc.) associated with the entity.

In some examples, an index may link an identifier of an entity (such as patient 610, relative 620, medical care provider 630, insurer 640, regulator 650, researcher 660, facilitator 670, etc.) to other entities (such as patient 610, relative 620, medical care provider 630, insurer 640, regulator 650, researcher 660, facilitator 670, and so forth). For example, an index may link an identifier of a patient 610 to relatives 620 related to the patient, medical care providers 630 that created and/or hold at least part of the records associated with the patient, to medical care providers 630 that hold permissions to access and/or edit at least parts of the records associated with the patient, to medical care providers 630 that accessed and/or edited at least parts of the records associated with the patient, to one or more insurers 640 associated with the patient, to regulators 650 dealing with medical information related to the patient, to researchers 660 studying medical information related to the patient, and so forth. For example, an index may link an identifier of a relative 620 to a patient 610 related to the relative and/or to entities associated with that patient. For example, an index may link an identifier of a medical care provider 630 to patients 610 and/or relatives of patient 620 that the medical care provider treat and/or has permissions to access and/or edit at least part of their medical records, to other medical care providers 630 that work in conjunction with the medical care provider, to insurer 640 of the medical care provider and/or patients of the medical care provider and/or employees of the medical care provider and/or suppliers of the medical care provider, to regulators 650 supervising the medical care provider, to researchers 660 working with and/or for the medical care provider, and so forth. For example, an index may link an identifier of an insurer 640 to entities insured by the insurer. For example, an index may link an identifier of a regulator 650 to entities supervised by the regulator. For example, an index may link an identifier of a researcher 660 to entities studied by the researcher, to entities working in conjunction with the researcher, and so forth. For example, an index may link an identifier of a facilitator 670 to entities recognized by and/or associated with the facilitator.

In some embodiments, identifiers 714 may comprise identifiers of entities (such as patients 610, relatives 620, medical care providers 630, insurers 640, regulators 650, researchers 660, facilitators 670, etc.) and/or records (such as medical records 702 scheduling records 704, financial records 706, insurance records 708, research records 710, indexes 712, permissions 716, and so forth). In some examples, identifier of an entity and/or record may be unique, while in other examples more than one identifier may identify the same entity and/or record.

In some embodiments, permissions 716 may specify which entities (such as patients 610, relatives 620, medical care providers 630, insurers 640, regulators 650, researchers 660, facilitators 670, etc.) may create and/or edit and/or access which records (such as medical records 702 scheduling records 704, financial records 706, insurance records 708, research records 710, indexes 712, identifiers 714, permissions 716, and so forth). For example, permissions 716 may comprise a group or entities allowed to create and/or edit and/or access selected records, a group or entities prohibited from creating and/or editing and/or accessing selected records, and so forth. For example, the selected records above may be specified as a group of records, as a rule defining a group of records, as the records associated with selected entities, and so forth. In some examples, permissions 716 may further specify which entities are allowed to grant which permission to which other entities regarding which records.

In some embodiments, medical care providers 630 may create and/or edit records of a patient 610 (such as medical records 702 scheduling records 704, financial records 706, insurance records 708, research records 710, indexes 712, identifiers 714, permissions 716, and so forth). These records may be indexed in indexes 712. These records may be accessed and/or edited by the patient, by some relatives 620 of the patient, by other medical care providers 630 treating the patient, by insurers 640 of the patient and/or the medical care provider, and so forth.

In some embodiments, an insurer 640 may access and/or edit and/or create records (such as medical records 702 scheduling records 704, financial records 706, insurance records 708, research records 710, indexes 712, identifiers 714, permissions 716, etc.) of entities (such as patients 610, relatives 620, medical care providers 630, other insurers 640, regulators 650, researchers 660, facilitators 670, etc.) insured by the insurer.

In some embodiments, a regulator 650 may access and/or edit and/or create records (such as medical records 702 scheduling records 704, financial records 706, insurance records 708, research records 710, indexes 712, identifiers 714, permissions 716, etc.) of entities (such as patients 610, relatives 620, medical care providers 630, other insurers 640, regulators 650, researchers 660, facilitators 670, etc.) supervised by the regulator.

In some embodiments, a researcher 660 may access and/or edit and/or create records (such as medical records 702 scheduling records 704, financial records 706, insurance records 708, research records 710, indexes 712, identifiers 714, permissions 716, etc.) of entities (such as patients 610, relatives 620, medical care providers 630, other insurers 640, regulators 650, researchers 660, facilitators 670, etc.) studied by the researcher.

In some embodiments, a facilitator 670 may access and/or edit and/or create records (such as medical records 702 scheduling records 704, financial records 706, insurance records 708, research records 710, indexes 712, identifiers 714, permissions 716, etc.) of entities (such as patients 610, relatives 620, medical care providers 630, other insurers 640, regulators 650, researchers 660, facilitators 670, and so forth). For example, a facilitator 670 may create an identifier 714, may verify an identity 714, and so forth. For example, a facilitator 670 may provide permission to relatives 620 of a patient 610 to access the patient's record after the death of the patient by editing permissions 716. For example, a facilitator 670 may recognize an entity as a licensed medical professional, as a licensed insurer, as a legitimate researcher, as a legal regulator, and so forth.

In some embodiments, access to a record and/or creation of a record and/or edition to a record may be recorded, for example in a log, in indexes 712, in the accessed and/or created and/or edited record, and so forth.

Figures 7B, 7C:
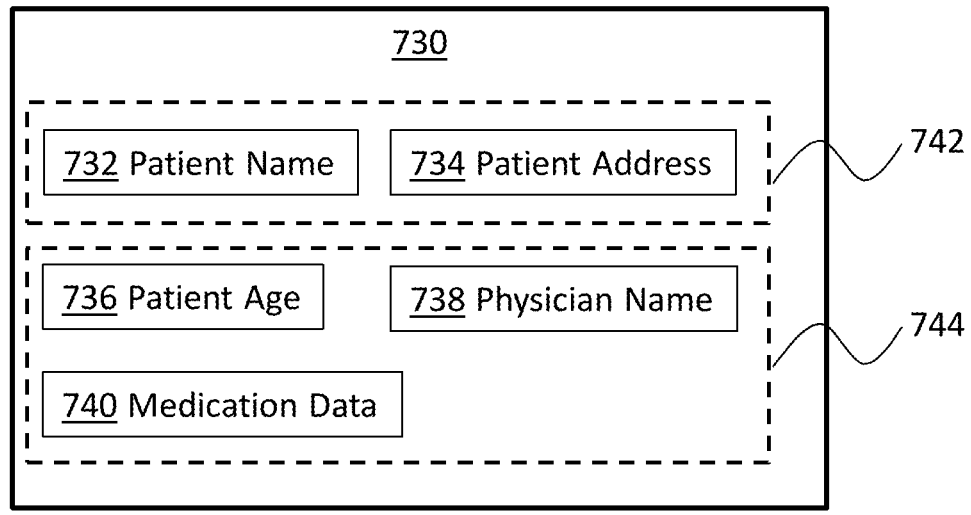
FIG. 7B illustrates an exemplary embodiment of a data element.
FIG. 7C illustrates an exemplary embodiment of a data element.

FIG. 7B illustrates an exemplary embodiment of a data element 730. In some examples, data element 730 may be stored in a memory unit (such as memory 700), in a database, in a data structure, in a table, and so forth. In some examples, data element 730 may comprise one or more data fields. For example, in the example of FIG. 7B data element 730 may comprise patient name 732, patient address 734, patient age 736, physician name 738 and medication data 740. In some examples, data element 730 may include portion 742 that includes identifiable information of a patient (in this example, portion 742 may include data fields patient name 732 and patient address 734), and portion 744 that does not include identifiable information of a patient (in this example, portion 744 may include data fields patient age 736, physician name 738 and medication data 740). In some examples, data element 730 may include additional portions and/or data fields that are not included in portion 742 and portion 744.

FIG. 7C illustrates an exemplary embodiment of a data element 750. In some examples, data element 750 may be stored in a memory unit (such as memory 700), in a database, in a data structure, in a table, and so forth. In some examples, data element 750 may comprise a table including one or more columns. For example, in the example of FIG. 7C data element 750 may comprise patient name column 752, patient phone number column 754, physician name 756 and appointment time 758. In some examples, data element 750 may include portions that includes identifiable information of a patient and portions that does not include identifiable information of a patient. The division of data element 750 to portions that includes identifiable information of a patient and portions that does not include identifiable information of a patient may be based on the type of the column (for example, patient name column 752 and patient phone number column 754 may be identified as including identifiable information of a patient based on the type of the column), may be based on a distribution of values in the column (for example, in clinics that only have one or few appointments at the same time, appointment time column 758 may be identified as including identifiable information of a patient based on the distribution of appointment times in the column, while in clinics that have many appointments at the same time, appointment time column 758 may be identified as not including identifiable information of a patient based on the distribution of appointment times in the column), may be based on values in the column (for example, a comparison of values in patient name column 752 with a dictionary may indicates that the values include names, and therefore patient name column 752 be identified as including identifiable information of a patient), may be based on analysis of values in the column and/or in other columns (for example using a machine learning model trained using training examples), and so forth.

In some embodiments, an identified copy of the data element and a de-identified copy of the data element may be used, for example as described below. For example, the identified copy of the data element may include identified information of a patient, and the de-identified copy of the data element may include no identified information of a patient. In the examples of FIG. 7B and FIG. 7C, any one of data element 730 and data element 750 includes identified information of a patient, and therefore data element 730 and data element 750 are identified copies. In one example, de-identified copies of data element 730 and data element 750 may include data fields that comprise no identified information of a patient and may exclude fields that comprise identified information of a patient. For example, a de-identified copy of data element 730 may include portion 744 of data element 730 and may not include any part of portion 742 of data element 730. In another example, a de-identified copy of data element 730 may include data field 756 but not data fields 752 and 754, and may include or not include data field 758 based on whether data field 758 includes identified information of a patient (for example, as determined as described above). In one example, the identified copy and/or the de-identified copy may be obtained by accessing the identified copy and/or the de-identified copy in a memory (such as memory units 210, shared memory modules 410, and so forth). In another example, the identified copy and/or the de-identified copy may be received from an external device over a communication network using a communication device (such as communication modules 230, internal communication modules 440, external communication modules 450, etc.), may be received from a user, and so forth. In some examples, the identified copy may be analyzed to generate the de-identified copy. For example, a machine learning model may be trained using training example to generate de-identified copies of data sources that includes identified information, and the trained machine learning model may be used to analyze a data element and generate a de-identified copy of data element. An example of such training example may include a sample data element together with a desired de-identified copy of the sample data element. In another example, the identified copy may include a plurality of fields, for each field it may be determined whether the field includes identified information of a patient (for example as described above), and fields that are determined to not include identified information of a patient may be included in the de-identified copy, while fields that are determined to include identified information of a patient may be omitted from the de-identified copy.

In some embodiments, a method, such as methods 800, 820, 840, 900, 920, 1000, etc., may comprise of one or more steps. In some examples, a method, as well as all individual steps therein, may be performed by various aspects of computing device 200, cloud platform 400, computational node 500, and so forth. For example, the method may be performed by processing units 220 executing software instructions stored within memory units 210 and/or within shared memory modules 410. In some examples, a method, as well as all individual steps therein, may be performed by a dedicated hardware. In some examples, computer readable medium (such as a non-transitory computer readable medium) may store data and/or computer implementable instructions for carrying out a method. Some examples of possible execution manners of a method may include continuous execution (for example, returning to the beginning of the method once the method normal execution ends), periodically execution, executing the method at selected times, execution upon the detection of a trigger (some examples of such trigger may include a trigger from a user, a trigger from another method, a trigger from an external device, etc.), and so forth.

In some embodiments, machine learning algorithms (also referred to as machine learning models in the present disclosure) may be trained using training examples, for example in the cases described below. Some examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear algorithms, non-linear algorithms, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by an process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters.

In some embodiments, trained machine learning algorithms (also referred to as trained machine learning models in the present disclosure) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

A convolution may include a convolution of any dimension. A one-dimensional convolution is a function that transforms an original sequence of numbers to a transformed sequence of numbers. The one-dimensional convolution may be defined by a sequence of scalars. Each particular value in the transformed sequence of numbers may be determined by calculating a linear combination of values in a subsequence of the original sequence of numbers corresponding to the particular value. A result value of a calculated convolution may include any value in the transformed sequence of numbers. Likewise, an n-dimensional convolution is a function that transforms an original n-dimensional array to a transformed array. The n-dimensional convolution may be defined by an n-dimensional array of scalars (known as the kernel of the n-dimensional convolution). Each particular value in the transformed array may be determined by calculating a linear combination of values in an n-dimensional region of the original array corresponding to the particular value. A result value of a calculated convolution may include any value in the transformed array. In some examples, an image may comprise one or more components (such as color components, depth component, etc.), and each component may include a two-dimensional array of pixel values. In one example, calculating a convolution of an image may include calculating a two-dimensional convolution on one or more components of the image. In another example, calculating a convolution of an image may include stacking arrays from different components to create a three-dimensional array, and calculating a three-dimensional convolution on the resulting three-dimensional array. In some examples, a video may comprise one or more components (such as color components, depth component, etc.), and each component may include a three-dimensional array of pixel values (with two spatial axes and one temporal axis). In one example, calculating a convolution of a video may include calculating a three-dimensional convolution on one or more components of the video. In another example, calculating a convolution of a video may include stacking arrays from different components to create a four-dimensional array, and calculating a four-dimensional convolution on the resulting four dimensional array.

In some embodiments, analyzing audio data (for example, by the methods, steps and modules described herein) may comprise analyzing the audio data to obtain a preprocessed audio data, and subsequently analyzing the audio data and/or the preprocessed audio data to obtain the desired outcome. One of ordinary skill in the art will recognize that the followings are examples, and that the audio data may be preprocessed using other kinds of preprocessing methods. In some examples, the audio data may be preprocessed by transforming the audio data using a transformation function to obtain a transformed audio data, and the preprocessed audio data may comprise the transformed audio data. For example, the transformation function may comprise a multiplication of a vectored time series representation of the audio data with a transformation matrix. For example, the transformation function may comprise convolutions, audio filters (such as low-pass filters, high-pass filters, band-pass filters, all-pass filters, etc.), linear functions, nonlinear functions, and so forth. In some examples, the audio data may be preprocessed by smoothing the audio data, for example using Gaussian convolution, using a median filter, and so forth. In some examples, the audio data may be preprocessed to obtain a different representation of the audio data. For example, the preprocessed audio data may comprise: a representation of at least part of the audio data in a frequency domain; a Discrete Fourier Transform of at least part of the audio data; a Discrete Wavelet Transform of at least part of the audio data; a time/frequency representation of at least part of the audio data; a spectrogram of at least part of the audio data; a log spectrogram of at least part of the audio data; a Mel-Frequency Spectrum of at least part of the audio data; a sonogram of at least part of the audio data; a periodogram of at least part of the audio data; a representation of at least part of the audio data in a lower dimension; a lossy representation of at least part of the audio data; a lossless representation of at least part of the audio data; a time order series of any of the above; any combination of the above; and so forth. In some examples, the audio data may be preprocessed to extract audio features from the audio data. Some non-limiting examples of such audio features may include: auto-correlation; number of zero crossings of the audio signal; number of zero crossings of the audio signal centroid; MP3 based features; rhythm patterns; rhythm histograms; spectral features, such as spectral centroid, spectral spread, spectral skewness, spectral kurtosis, spectral slope, spectral decrease, spectral roll-off, spectral variation, etc.; harmonic features, such as fundamental frequency, noisiness, inharmonicity, harmonic spectral deviation, harmonic spectral variation, tristimulus, etc.; statistical spectrum descriptors; wavelet features; higher level features; perceptual features, such as total loudness, specific loudness, relative specific loudness, sharpness, spread, etc.; energy features, such as total energy, harmonic part energy, noise part energy, etc.; temporal features; and so forth. In some examples, analyzing the audio data may include calculating at least one convolution of at least a portion of the audio data, and using the calculated at least one convolution to calculate at least one resulting value and/or to make determinations, identifications, recognitions, classifications, and so forth.

In some embodiments, analyzing audio data (for example, by the methods, steps and modules described herein) may comprise analyzing the audio data and/or the preprocessed audio data using one or more rules, functions, procedures, artificial neural networks, speech recognition algorithms, speaker recognition algorithms, speaker diarization algorithms, audio segmentation algorithms, noise cancelling algorithms, source separation algorithms, inference models, and so forth. Some non-limiting examples of such inference models may include: an inference model preprogrammed manually; a classification model; a data regression model; a result of training algorithms, such as machine learning algorithms and/or deep learning algorithms, on training examples, where the training examples may include examples of data instances, and in some cases, a data instance may be labeled with a corresponding desired label and/or result; and so forth.

Some non-limiting examples of image data (also referred to as visual data herein) may include images, grayscale images, color images, 2D images, 3D images, videos, 2D videos, 3D videos, frames, footages, data derived from other image data, and so forth. In some embodiments, analyzing image data (for example by the methods, steps and modules described herein) may comprise analyzing the image data to obtain a preprocessed image data, and subsequently analyzing the image data and/or the preprocessed image data to obtain the desired outcome. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may comprise the transformed image data. For example, the transformed image data may comprise one or more convolutions of the image data. For example, the transformation function may comprise one or more image filters, such as low-pass filters, high-pass filters, band-pass filters, all-pass filters, and so forth. In some examples, the transformation function may comprise a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may comprise: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may comprise information based on and/or related to the extracted edges. In some examples, the image data may be preprocessed to extract image features from the image data. Some non-limiting examples of such image features may comprise information based on and/or related to: edges; corners; blobs; ridges; Scale Invariant Feature Transform (SIFT) features; temporal features; and so forth. In some examples, analyzing the image data may include calculating at least one convolution of at least a portion of the image data, and using the calculated at least one convolution to calculate at least one resulting value and/or to make determinations, identifications, recognitions, classifications, and so forth.

In some embodiments, analyzing image data (for example by the methods, steps and modules described herein) may comprise analyzing the image data and/or the preprocessed image data using one or more rules, functions, procedures, artificial neural networks, object detection algorithms, face detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth. In some embodiments, analyzing image data (for example by the methods, steps and modules described herein) may comprise analyzing pixels, voxels, point cloud, range data, etc. included in the image data.

FIG. 8A illustrates an example of a method 800 for hybrid differential privacy. In this example, method 800 may comprise: receiving a first query, a second query and a third query associated with medical data (Step 802); accessing the medical data to determine a possible response to the first query, a possible response to the second query, and a possible response to the third query (Step 804); determining a first privacy loss level associated with the possible response to the first query, a second privacy loss level associated with the possible response to the second query, and a third privacy loss level associated with the possible response to the third query (Step 806), the first privacy loss level and the second privacy loss level may be identical; determining a first confidence level for the determination of the first privacy loss level, and a second confidence level for the determination of the second privacy loss level (Step 808), the second confidence level is lower than the first confidence level; in response to the first privacy loss level and the first confidence level, providing the possible response to the first query (Step 810); in response to the third privacy loss level, avoiding providing the possible response to the third query (Step 812); and in response to the second privacy loss level and the second confidence level, involve a manual review in the determination of whether to provide or to avoid providing the possible response to the second query (814), for example using method 820. In some implementations, method 800 may comprise one or more additional steps, while some of the steps listed above may be modified or excluded. In some implementations, one or more steps illustrated in FIG. 8A may be executed in a different order and/or one or more groups of steps may be executed simultaneously and/or a plurality of steps may be combined into single step and/or a single step may be broken down to a plurality of steps.

FIG. 8B illustrates an example of a method 820 for involving manual review in the determination of whether to provide or to avoid providing the possible response to a query. In this example, method 820 may comprise: providing to a user information indicative of at least one aspect of the possible response to a particular query (Step 822); receiving an input from the user (Step 824); and determining whether to provide or to avoid providing the possible response to the particular query based on the input received from the user (Step 826). In some implementations, method 820 may comprise one or more additional steps, while some of the steps listed above may be modified or excluded. In some implementations, one or more steps illustrated in FIG. 8B may be executed in a different order and/or one or more groups of steps may be executed simultaneously and/or a plurality of steps may be combined into single step and/or a single step may be broken down to a plurality of steps.

FIG. 8C illustrates an example of a method 840 for hybrid differential privacy. In this example, method 840 may comprise: receiving a fourth query associated with the medical data (Step 842); accessing the medical data to determine a possible response to the fourth query (Step 844); determining a fourth privacy loss level associated with the possible response to the fourth query (Step 846), the fourth privacy loss level may be identical to the first privacy loss level and the second privacy loss level; determining a fourth confidence level for the determination of the fourth privacy loss level (Step 848), the fourth confidence level may be between the second confidence level and the first confidence level; accessing users availability data (Step 850); and in response to the fourth privacy loss level and the fourth confidence level, determining based on the users availability data whether to involve a manual review in a determination of whether to provide the possible response to the fourth query (Step 852). In some implementations, method 840 may comprise one or more additional steps, while some of the steps listed above may be modified or excluded. In some implementations, one or more steps illustrated in FIG. 8C may be executed in a different order and/or one or more groups of steps may be executed simultaneously and/or a plurality of steps may be combined into single step and/or a single step may be broken down to a plurality of steps. In some implementations, any of the steps of method 840 may be executed before, after or simultaneously with method 800.

In some examples, Step 802 may include receiving a first query, a second query and a third query associated with medical data. In some examples, Step 842 may include receiving a fourth query associated with the medical data. Some non-limiting examples of such medical data may comprise at least one of private medical data 112, public data 120, proprietary medical data 142, medical records 702, scheduling records 704, financial records 706, insurance records 708, research records 710, indexes 712, identifiers 714, data elements 730 (or parts thereof), data elements 750 (or parts thereof), and so forth. In some examples, receiving a query (such as the first, second, third or fourth query) may comprise at least one of reading the query from memory (for example, from memory unit 210, from shared memory module 410, from memory 700, etc.), receiving the query from an external device (for example, from computerized data analysis device 144, from a computing device such as computing device 200, from cloud platform 400, etc.), receiving the query from a user (for example, through a user interface, through voice commands, through gesture recognition, etc.), receiving the query over a communication network (for example over communication network 130, using communication module 230, using internal communication module 440, using external communication module 450, etc.), and so forth. In some examples, a query (such as the first, second, third or fourth query) may comprise a question and/or a search criteria. The question and/or the search criteria may relate to a particular collection of data. Some non-limiting examples of a query may include 'does the particular collection of data include psoriasis patients treated with vedolizumab?', 'what is the ratio of psoriasis patients that also suffer from Crohn's disease (in the particular collection of data)?', 'who are the patients that in the particular collection of data that suffer from Crohn's disease and are treated with vedolizumab?', and so forth.

In some examples, receiving a query (for example, receiving the first query, the second query and the third query by Step 802) may comprise accessing one or more streams of digital communication sent among computing devices, and analyzing the one or more streams to detect the query (for example, to detect the first query, the second query and the third query) in the one or more streams. For example, the one or more streams of digital communication may be one or more streams of digital communication sent over communication network 130. In another example, the one or more streams of digital communication may be one or more streams of digital communication sent from computerized data analysis device 144 to a computerized device (such as computing device 200) or to a cloud platform (such as cloud platform 400). In one example, the one or more streams of digital communication may include communication in a specific protocol, and the communication may be parsed based on the specific protocol to identify the query. In another example, the one or more streams of digital communication may include an encoding of the query (such as a compressed encoding of the query, an encrypted encoding of the query, etc.), and the encoding of the query may be decoded to receive the query (for example, uncompressed, decrypted, etc.).

In some examples, Step 804 may comprise accessing the medical data to determine a possible response to the first query received by Step 802, a possible response to the second query received by Step 802, and a possible response to the third query received by Step 802. In some examples, Step 844 may comprise accessing the medical data to determine a possible response to the fourth query received by Step 842. In some examples, accessing a collection of data (such as the medical data) may comprise at least one of accessing the collection of data in memory (for example, from memory unit 210, from shared memory module 410, from memory 700, etc.), accessing the collection of data via an external device (for example, via computerized data analysis device 144, via a computing device such as computing device 200, via cloud platform 400, etc.), over a communication network (for example over communication network 130, using communication module 230, using internal communication module 440, using external communication module 450, etc.), and so forth. In some examples, accessing a collection of data (such as the medical data) may comprise at least one of obtaining information from the collection of data, analyzing information included in the collection of data, making one or more determinations based on information included in the collection of data, or modifying information in the collection of data. In some examples, accessing a collection of data (such as the medical data) to determine a possible response to a query (such as the first, second, third or fourth query) may comprise, in response to a first information included in the collection of data, determining one possible response to the query, and in response to a second information included in the collection of data, determining a different possible response to the query. In some examples, accessing a collection of data (such as the medical data) to determine a possible response to a query (such as the first, second, third or fourth query) may comprise analyzing information included in the collection of data to determine the possible response to the query, for example using an inference model, using an algorithm, using a function, using a classification model, using a regression model, using an artificial neural network, using a trained machine learning model, and so forth.

In some examples, Step 806 may comprise determining a first privacy loss level associated with the possible response to the first query, a second privacy loss level associated with the possible response to the second query, and/or a third privacy loss level associated with the possible response to the third query. In some examples, Step 846 may comprise determining a fourth privacy loss level associated with the possible response to the fourth query. In one example, the first privacy loss level and the second privacy loss level may be identical. In another example, the first privacy loss level and the second privacy loss level may be different (for example, the first privacy loss level may be lower than the second privacy loss level, or the first privacy loss level may be higher than the second privacy loss level). The third privacy loss level may be different from the first privacy loss level and from the second privacy loss level, may be identical to the first privacy loss level and to the second privacy loss level, or may be identical to only one of the first privacy loss level and the second privacy loss level. In one example, the fourth privacy loss level may be identical to the first privacy loss level and to the second privacy loss level. In other example, the fourth privacy loss level may be different from the first privacy loss level and from the second privacy loss level, or may be identical to only one of the first privacy loss level and the second privacy loss level. Further, the fourth privacy loss level may be identical to the third privacy loss level, or may be different from the third privacy loss level. In some examples, a privacy loss level associated with a possible response to a query (for example, the first, second, third or fourth privacy loss level) may be a numerical privacy loss level (such as a number in a particular range or group of numbers, a percent, a ratio, etc.), may be a discrete value (such as 'high', 'medium', 'low', etc.), and so forth. In some examples, determining a privacy loss level associated with a possible response to a query (for example, the first, second, third or fourth privacy loss level) may comprise measuring the level of private information in the possible response to the query. In some examples, determining a privacy loss level associated with a possible response to a query (for example, the first, second, third or fourth privacy loss level) may comprise measuring the level of private information in the possible response to the query that is not already known to an entity associated with the query. In some examples, determining a privacy loss level associated with a possible response to a query (for example, the first, second, third or fourth privacy loss level) may comprise analyzing at least one of the query, the possible response to the query, the data collection associated with the query (such as the medical data), or the process of determining the possible response to the query to determine the privacy loss level associated with the possible response to the query. For example, a machine learning model may be trained using training examples to determine privacy loss levels associated with possible responses to queries. An example of such training example may include a label indicative of a privacy loss level associated with a sample possible response to a sample query, together with at least one of the sample query, the sample possible response to the sample query, a sample data collection associated with the sample query, or a characteristic of a sample process for determining the sample possible response to the sample query. In one example, Step 806 may use the trained machine learning model to determine the first privacy loss level via analysis of at least one of the first query, the possible response to the first query, the medical data, or the process of determining the possible response to the first query. In one example, Step 806 may use the trained machine learning model to determine the second privacy loss level via analysis of at least one of the second query, the possible response to the second query, the medical data, or the process of determining the possible response to the second query. In one example, Step 806 may use the trained machine learning model to determine the third privacy loss level via analysis of at least one of the third query, the possible response to the third query, the medical data, or the process of determining the possible response to the third query. In one example, Step 846 may use the trained machine learning model to determine the fourth privacy loss level via analysis of at least one of the fourth query, the possible response to the fourth query, the medical data, or the process of determining the possible response to the fourth query.

In some example, a privacy loss level associated with a possible response to a query may be based on a source of the query. For example, the first privacy loss level determined by Step 806 may be based on a source of the first query received by Step 802, the second privacy loss level determined by Step 806 may be based on a source of the second query received by Step 802, and/or the third privacy loss level determined by Step 806 may be based on a source of the third query received by Step 802. In another example, the fourth privacy loss level determined by Step 846 may be based on a source of the fourth query received by Step 842. In one example, a source of a query may be an entity that generated the query, may be an entity that provided the query, may be an entity that transmitted the query, may be an entity configured to receive responses to the query, and so forth. In one example, in response to one source of the query, one privacy loss level associated with the possible response to the query may be determined (for example, by Step 806 or by Step 846), and in response to the same possible response and a different source of the same query, a different privacy loss level associated with the possible response to the query may be determined (for example, by Step 806 or by Step 846). In some examples, the privacy loss level may be based on historic queries associated with the source of the query (for example, the first privacy loss level may be based on historic queries associated with a source of the first query). For example, when the historic queries associated with the source includes an identical or a similar query, the determined privacy loss level may be lower. In some examples, the privacy loss level may be based on responses to historic queries associated with a source of the query (for example, the first privacy loss level may be based on responses to historic queries associated with a source of the first query). For example, when the responses to historic queries associated with the source includes at least part of the information that causes the privacy loss in the possible response to the query, the determined privacy loss level may be lower.

In some examples, Step 808 may comprise determining a first confidence level for the determination of the first privacy loss level, and a second confidence level for the determination of the second privacy loss level. In some examples, Step 848 may comprise determining a fourth confidence level for the determination of the fourth privacy loss level. In one example, the second confidence level may be lower than the first confidence level. In other examples, the second confidence level may be identical to the first confidence level, or may be higher than the first confidence level. In one example, the fourth confidence level may be between the second confidence level and the first confidence level. In other examples, the fourth confidence level may be higher than the second confidence level and the first confidence level, may be lower than the second confidence level and the first confidence level, may be identical to at least one of the second confidence level or the first confidence level, and so forth. In some examples, a confidence level for the determination of a privacy loss level (for example, the first, second, third or fourth confidence level) may be a numerical confidence level (such as a number in a particular range or group of numbers, a percent, a ratio, etc.), may be a discrete value (such as 'high', 'medium', 'low', etc.), and so forth. In some examples, determining a confidence level for a determination of a privacy loss level associated with a possible response to a query (for example, determining the first, second, third or fourth confidence level) may comprise analyzing at least one of the query, the possible response to the query, the data collection associated with the query (such as the medical data), the process of determining the possible response to the query, or the privacy loss level to determine the confidence level for the determination of the privacy loss level. In some examples, likelihoods of different alternative privacy loss levels for the possible response to the query may be estimated, and the confidence level may be a function of these likelihoods. In some examples, a machine learning model may be used to determine the privacy loss level (for example, the first, second, third or fourth privacy loss level), for example as described above, and one of the outputs of the machine learning model may be indicative of the confidence level. For example, the machine learning model may be a regression model configured to output a confidence interval in addition to a value, the value may be the privacy loss level, and the confidence level may be a monotonically decreasing function of the width of the confidence interval. In another example, the machine learning model may be a classification model configured to provide class membership probabilities, where each class corresponds to a different privacy loss level, the class corresponding to the highest probability may determine the privacy loss level, and the confidence level may be a function of the probability corresponding to that class.

In some examples, the second query may be received by Step 802 after the providence by Step 810 of the possible response to the first query, and the determination of the second confidence level by Step 808 may be based on the possible response to the first query determined by Step 804 and provided by Step 810. For example, in response to one possible response to the first query, Step 808 may determine one level for the second confidence level, and in response to another possible response to the first query, Step 808 may determine another level for the second confidence level. In one example, when the possible response to the first query is identical to the possible response to the second query determined by Step 804, the second privacy loss level may be lower and/or the second confidence level may be higher than when the two differ. In another example, the possible response to the first query and the possible response to the second query determined by Step 804 may have a certain amount of information in common, and the Step 808 may determine the second confidence level based on the certain amount of information. In some examples, the first query and the second query received by Step 802 may be identical, the possible response to the first query and the possible response to the second query determined by Step 803 may be identical, and the second confidence level determined by Step 806 may be lower than the first confidence level determined by Step 806 due to the second query being received by Step 802 after the providence of the possible response to the first query by Step 810. For example, when the first query and the second query received by Step 802 are identical, and the possible response to the first query and the possible response to the second query determined by Step 803 are identical: when the second query being received by Step 802 after the providence of the possible response to the first query by Step 810, the second confidence level determined by Step 806 may be lower than the first confidence level determined by Step 806, and when the first query being received by Step 802 after a providence of the possible response to the second query, the second confidence level determined by Step 806 may be higher than the first confidence level determined by Step 806.

In some examples, a determination of a confidence level for a determination of a privacy loss level associated with a possible response to a query may be based on a source of the query. For example, the determination of the first confidence level by Step 808 may be based on a source of the first query, the determination of the second confidence level by Step 808 may be based on a source of the second query, and/or the determination of the third confidence level by Step 808 may be based on a source of the third query. In another example, the determination of the fourth confidence level by Step 848 may be based on a source of the fourth query. In one example, a source of a query may be an entity that generated the query, may be an entity that provided the query, may be an entity that transmitted the query, may be an entity configured to receive responses to the query, and so forth. In one example, in response to one source of the query, one confidence level associated with the possible response to the query may be determined (for example, by Step 808 or by Step 848), and in response to the same possible response and a different source of the same query, a different confidence level associated with the possible response to the query may be determined (for example, by Step 808 or by Step 848).

In some examples, a possible response to a query (such as the first, second, third or fourth query) may include an image, and the determination of a confidence level for a determination of a privacy loss level associated with a possible response to the query may be based on a result value of a calculated convolution of the image. For example, the possible response to the second query determined by Step 804 may include an image, and the determination of the second confidence level by Step 808 may be based on a result value of a calculated convolution of the image. For example, a convolution of at least part of the image may be calculated to obtain a result value of the calculated convolution of the at least part of the image, in response to one result value of the calculated convolution, Step 808 may determine one level for the second confidence level, and in response to another result value of the calculated convolution, Step 808 may determine another level for the second confidence level.

In some examples, Step 810 may comprise, for example in response to the first privacy loss level determined by Step 806 and the first confidence level determined by Step 808, providing the possible response to the first query (that is, the possible response determined by Step 804 to the first query received by Step 802). For example, method 800 may take Step 810 when, (i) the first privacy loss level determined by Step 806 and the second privacy loss level determined by Step 806 are identical, and (ii) the second confidence level determined by Step 808 is lower than the first confidence level determined by Step 808. In other examples, Step 810 may be used under other circumstances.

In some examples, providing a possible response to a query (for example, providing the possible response to the first query by Step 810, providing an alternative response to the query, etc.) may comprise storing the possible response in memory (for example, in memory unit 210, in shared memory module 410, in memory 700, etc.), for example at a specific location in the memory that enables another process or device to access the possible response. In some examples, providing a possible response to a query (for example, providing the possible response to the first query by Step 810, providing an alternative response to the query, etc.) may comprise at least one of providing the possible response to an external device (for example, to computerized data analysis device 144, to a computing device such as computing device 200, to cloud platform 400, etc.), providing the possible response to a user (for example, through a user interface, visually, audibly, textually, numerically, graphically, etc.), or providing the possible response over a communication network (for example over communication network 130, using communication module 230, using internal communication module 440, using external communication module 450, etc.).

In some examples, Step 812 may comprise, for example in response to the third privacy loss level determined by Step 806, avoiding providing the possible response to the third query (that is, the possible response determined by Step 804 to the third query received by Step 802). For example, method 800 may take Step 812 when, (i) the first privacy loss level determined by Step 806 and the second privacy loss level determined by Step 806 are identical, and (ii) the second confidence level determined by Step 808 is lower than the first confidence level determined by Step 808. In other examples, Step 812 may be used under other circumstances.

In some examples, Step 814 may comprise, for example in response to the second privacy loss level determined by Step 806 and the second confidence level determined by Step 808, involving a manual review in the determination of whether to provide or to avoid providing the possible response to the second query, for example using method 820. In one example, Step 814 may comprise, for example in response to the second privacy loss level determined by Step 806 and the second confidence level determined by Step 808, providing to a user information indicative of at least one aspect of the possible response to the second query (as described in relation to Step 822), receiving an input from the user (as described in relation to Step 824), and determining whether to provide or to avoid providing the possible response to the second query based on the input received from the user (as described in relation to Step 826). In one example, method 800 may take Step 814 when, (i) the first privacy loss level determined by Step 806 and the second privacy loss level determined by Step 806 are identical, and (ii) the second confidence level determined by Step 808 is lower than the first confidence level determined by Step 808. In other examples, Step 814 may be used under other circumstances.

In some examples, Step 850 may comprise accessing users availability data. For example, the users availability data may comprise at least one of an indication that one or more users (for example, of a group of users) are currently available for manual review, an indication that one or more users of a group of users are currently unavailable for manual review, a future availability schedule of at least one user, a future unavailability schedule of at least one user, an indication of availability (current and/or future) of at least one user for a particular type of manual review, or an indication of unavailability (current and/or future) of at least one user for a particular type of manual review. In some examples, accessing the users availability data by Step 850 may comprise at least one of reading the users availability data from memory (for example, from memory unit 210, from shared memory module 410, from memory 700, etc.), receiving the users availability data from an external device (for example, from computerized data analysis device 144, from a computing device such as computing device 200, from cloud platform 400, etc.), receiving the users availability data from a person (for example, through a user interface, through voice commands, through gesture recognition, etc.), receiving the users availability data over a communication network (for example over communication network 130, using communication module 230, using internal communication module 440, using external communication module 450, etc.), determining the users availability data by analyzing a calendar, and so forth. In one example, method 840 may take Step 850 when, (i) the first privacy loss level determined by Step 806, the second privacy loss level determined by Step 806 and the fourth privacy loss level determined by Step 846 are identical, and (ii) the second confidence level determined by Step 808 is lower than the first confidence level determined by Step 808, and (iii) the fourth confidence level is between the second confidence level and the first confidence level. In other examples, Step 850 may be used under other circumstances.

In some examples, Step 852 may comprise, for example in response to the fourth privacy loss level determined by Step 846 and the fourth confidence level determined by Step 848, determining based on the users availability data accessed by Step 850 whether to involve manual review in a determination of whether to provide or to avoid providing the possible response to the fourth query (that is, the possible response determined by Step 844 to the fourth query received by Step 842). In one example, method 840 may take Step 852 when, (i) the first privacy loss level determined by Step 806, the second privacy loss level determined by Step 806 and the fourth privacy loss level determined by Step 846 are identical, and (ii) the second confidence level determined by Step 808 is lower than the first confidence level determined by Step 808, and (iii) the fourth confidence level is between the second confidence level and the first confidence level. In other examples, Step 852 may be used under other circumstances. In some examples, when the users availability data accessed by Step 850 indicates that at least one user is available for manual review (for example, currently, at a given time period, for a manual review of a particular type, etc.), Step 852 may involve manual review in the determination of whether to provide or to avoid providing the possible response to the fourth query (for example using method 820), and when the users availability data accessed by Step 850 indicates that no user is available for manual review (for example, currently, at a given time period, for a manual review of a particular type, etc.), Step 852 may avoid involving manual review in the determination of whether to provide or to avoid providing the possible response to the fourth query (and may make the determination automatically, for example based on a default settings). In some examples, when the users availability data accessed by Step 850 indicates that a number of users available for manual review (for example, currently, at a given time period, for a manual review of a particular type, etc.) is above a selected threshold, Step 852 may involve manual review in the determination of whether to provide or to avoid providing the possible response to the fourth query (for example using method 820), and when the users availability data accessed by Step 850 indicates that the number of users available for manual review is below the selected threshold, Step 852 may avoid involving manual review in the determination of whether to provide or to avoid providing the possible response to the fourth query (and may make the determination automatically, for example based on a default settings). For example, the selected threshold may be configurable, may be a selected based on a total number of users, may be selected based on a load of queries, may be selected based on the fourth privacy loss level determined by Step 846, may be selected based on the fourth confidence level determined by Step 848, and so forth. In some examples, when Step 852 determine to involve manual review in the determination of whether to provide the possible response to the fourth query, method 840 may further comprise, providing to a user information indicative of at least one aspect of the possible response to the fourth query (as described in relation to Step 822), receiving an input from the user (as described in relation to Step 824), and determining whether to provide or to avoid providing the possible response to the fourth query based on the input received from the user (as described in relation to Step 826).

In some examples, Step 822 may comprise providing to a user information indicative of at least one aspect of a possible response to a query (for example, at least one aspect of the possible response determined by Step 804 to the second query received by Step 802, at least one aspect of the possible response determined by Step 844 to the fourth query received by Step 842, and so forth). For example, the information indicative of the at least one aspect may be provided to the user through a user interface, visually, audibly, textually, numerically, graphically, via another process or an external device, and so forth. Some non-limiting examples of such at least one aspect of a possible response to a query may include the possible response, the query, at least part of a data collection associated with the query (such as the medical data), a determined privacy loss level associated with the possible response to the query, a determined confidence level for the determination of the privacy loss level, an indication of an entity associated with the query, a history of queries and/or responses corresponding to the entity associated with the query, information based on an analysis of one or more of the above, and so forth. In some examples, a possible response to a query may include a plurality of elements, and the at least one aspect of the possible response to the query may be based on a distribution of the plurality of elements. For example, the possible response to the second query may include a plurality of elements, and the at least one aspect of the possible response to the second query may be based on a distribution of the plurality of elements. In one example, the at least one aspect may include a parameter of the distribution. For example, the distribution may be a normal distribution, and the parameter may be a mean, a variance, or a standard deviation. In another example, the distribution may be a Poisson distribution, and the parameter may be a degree of freedom. In yet another example, the distribution may be a chi-squared distribution, and the parameter may be a rate. In an additional example, the parameter may be at least one of a mean, a median, a mode, a variance, a standard deviation, a skewness, a location parameter, a dispersion, a scale parameter, or a shape parameter. In some examples, a possible response to a query may include an image, and the at least one aspect of the possible response to the query may be based on a result value of a calculated convolution of the image. For example, the possible response to the second query may include an image, and the at least one aspect of the possible response to the second query may be based on a result value of a calculated convolution of the image. For example, the at least one aspect of the possible response to the query may be the result value of the calculated convolution of the image, may be a function of the result value of the calculated convolution of the image, and so forth. Some non-limiting examples of such function may include a linear function, a non-linear function, a polynomial function, an exponential function, a logarithmic function, a continuous function, a non-continuous function, and so forth.

In some examples, Step 822 may further comprise selecting the user of a plurality of alternative users. In one example, the plurality of alternative users may be a configured group of users. In another example, the plurality of alternative users may be available users (for example, based on a user availability data, such as the user availability data received by Step 850). In some examples, Step 822 may further comprise selecting the user of the plurality of alternative users based on the query (for example, based on the second query, based on the fourth query, etc.). In one example, in response to one query, Step 822 may select one user of the plurality of alternative users, and in response to another query, Step 822 may select another user of the plurality of alternative users. In one example, each user of the plurality of alternative users may be associated with a particular type of queries, and the user may be selected based on the type of the query (for example, based on the type of the second query, based on the type of the fourth query, etc.). For example, a user corresponding to the type of the query may be selected. In one example, each user of the plurality of alternative users may be associated with affinities to different types of queries, and the user may be selected based on their affinities to the type of the query. For example, the available user with the maximal affinity may be selected. In some examples, Step 822 may further comprise selecting the user of the plurality of alternative users based on the possible response to the query (for example, based on the possible response to the second query, based on the possible response to the fourth query, etc.). In one example, in response to one possible response to the query, Step 822 may select one user of the plurality of alternative users, and in response to another possible response to the query, Step 822 may select another user of the plurality of alternative users. In one example, each user of the plurality of alternative users may be associated with a particular type of response, and the user may be selected based on the type of the possible response to the query (for example, based on the type of the possible response to the second query, based on the type of the possible response to the fourth query, etc.). For example, a user corresponding to the type of the possible response to the query may be selected. In one example, each user of the plurality of alternative users may be associated with affinities to different types of responses, and the user may be selected based on their affinities to the type of the possible response to the query. For example, the available user with the maximal affinity may be selected. In some examples, the user may be selected of the plurality of alternative users based on a source of the query (for example, based on a source of the second query, based on a source of the fourth query, etc.). In one example, in response to one source of the query, Step 822 may select one user of the plurality of alternative users, and in response to another source of the query, Step 822 may select another user of the plurality of alternative users. In one example, each user of the plurality of alternative users may be associated with a different group of entities, and the user may be selected based on the source of the query (for example, based on the source of the second query, based on the source of the fourth query, etc.). For example, a user corresponding to a group of entities that includes the source of the query may be selected. In one example, each user of the plurality of alternative users may be associated with affinities to different types of sources, and the user may be selected based on their affinities to the type of the source of the query. For example, the available user with the maximal affinity may be selected.

In some examples, Step 824 may comprise receiving an input from the user of Step 822, for example after providing the information to the user by Step 822 and/or in response to the information provided to the user by Step 822. For example, receiving the input from the user by Step 824 may comprise at least one of receiving the input through a user interface, receiving the input through voice commands, receiving the inputs through gestures, receiving the input through an input device (such as a keyboard, a computer mouse, a touchscreen, a joystick, a haptic glove, etc.), receiving the input through another process, or receiving the input through an external device. In one example, the input received from Step 824 may include a decision of the user (or an indication of the decision of the user) whether to provide or to avoid providing the possible response to the query (for example, whether to provide or to avoid providing the possible response to the second query, provide or to avoid providing the possible response to the fourth query, and so forth). In another example, the input received from Step 824 may include a selection of an alternative response to the query (for example, of an alternative response to the second query, of an alternative response to the fourth query, and so forth).

In some examples, Step 826 may comprise determining whether to provide or to avoid providing the possible response to the query (for example, the possible response to the second query, the possible response to the fourth query, etc.) based on the input received from the user by Step 824. For example, the input received from Step 824 may include a decision of the user whether to provide or to avoid providing the possible response to the query, as described above, and Step 826 may follow the decision of the user. In another example, decisions of a plurality of users may be obtained, for example by repeating Step 822 and Step 824 multiple times with different users, and Step 826 may use a voting algorithm to determine whether to provide or to avoid providing the possible response to the query based on the obtained decisions of the plurality of users.

In some examples, method 820 may further comprise, for example in response to the input received from of the user by Step 824, providing an alternative response to the query (for example, providing an alternative response to the second query, providing an alternative response to the fourth query, etc.). For example, the alternative response to the query may be provided as described above (for example, in relation to Step 810). In some examples, the alternative response to the query (for example, the alternative response to the second query, the alternative response to the fourth query, etc.) may be based on the input received from the user by Step 824. For example, the input received from Step 824 may include a selection of an alternative response to the query, and the selected alternative response to the query may be provided. In another example, the input received from Step 824 may include the alternative response to the query, and the alternative response to the query may be provided. In yet another example, the input received from Step 824 may include a modification to the possible response to the query (for example, a reduction of at least part of the possible response to the query, a change of at least one value in the possible response to the query, etc.), and the modified possible response to the query may be provided. In some examples, the alternative response to the query (for example, to the second query, to the fourth query, etc.) may be selected by the user from a plurality of optional responses to the query (for example, to the second query, to the fourth query, etc.). For example, at least part of the plurality of optional responses to the query may be presented to the user by Step 822, and the selection may be received from the user by Step 824.

FIG. 9A illustrates an example of a method 900 for assigning confidence to data de-identification. In this example, method 900 may comprise: accessing a data collection to generate a de-identified copy of the data collection (Step 902); determining a confidence level that the generated de-identified copy does not include identified information (Step 904); in response to a first value of the confidence level, providing particular information based on the de-identified copy of the data collection to a first entity and to a second entity (Step 906); and in response to a second value of the confidence level, providing the particular information to the first entity and forgoing providing the particular information to the second entity (Step 908). In some implementations, method 900 may comprise one or more additional steps, while some of the steps listed above may be modified or excluded. In some implementations, one or more steps illustrated in FIG. 9A may be executed in a different order and/or one or more groups of steps may be executed simultaneously and/or a plurality of steps may be combined into single step and/or a single step may be broken down to a plurality of steps.

FIG. 9B illustrates an example of a method 920 for assigning confidence to data de-identification. In this example, method 920 may comprise: analyzing a first image included in the data collection but not included in the de identified copy to determine a visual characteristic (Step 922); analyzing a second image included in the data collection and in the de-identified copy to determine a likelihood that the second image includes the visual characteristic (Step 924); and determining the confidence level that the generated de-identified copy does not include identified information based on the determined likelihood (Step 926). In some implementations, method 920 may comprise one or more additional steps, while some of the steps listed above may be modified or excluded. In some implementations, one or more steps illustrated in FIG. 9B may be executed in a different order and/or one or more groups of steps may be executed simultaneously and/or a plurality of steps may be combined into single step and/or a single step may be broken down to a plurality of steps.

In some examples, Step 902 may comprise accessing a data collection to generate a de-identified copy of the data collection. In one example, the data collection may include medical data. In another example, the data collection may include non-medical data. Some non-limiting examples of such data collection may comprise at least one of private medical data 112, public data 120, proprietary medical data 142, medical records 702, scheduling records 704, financial records 706, insurance records 708, research records 710, indexes 712, identifiers 714, data elements 730 (or parts thereof), data elements 750 (or parts thereof), and so forth. In some examples, accessing the data collection by Step 902 may comprise at least one of reading at least part of the data collection from memory (for example, from memory unit 210, from shared memory module 410, from memory 700, etc.), receiving at least part of the data collection from an external device (for example, from computerized data analysis device 144, from a computing device such as computing device 200, from cloud platform 400, etc.), receiving at least part of the data collection from a person (for example, through a user interface, through voice commands, through gesture recognition, etc.), receiving at least part of the data collection over a communication network (for example over communication network 130, using communication module 230, using internal communication module 440, using external communication module 450, etc.), and so forth. In some examples, accessing a data collection by Step 902 to generate the de-identified copy of the data collection may comprise analyzing the data collection to generate the de-identified copy of the data collection. For example, a machine learning model may be trained using training example to generate de-identified copies of data sources that includes identified information, and Step 902 may use the trained machine learning model to analyze a data collection and generate the de-identified copy of data collection. An example of such training example may include a sample data collection together with a desired de-identified copy of the sample data collection. In another example, the data collection may include a plurality of fields, for each field it may be determined whether the field includes identified information (for example as described above), and fields that are determined to not include identified information may be included in the de-identified copy of the data collection, while fields that are determined to include identified information may be omitted from the de-identified copy of the data collection. In yet another example, the data collection may include a plurality of data elements, and Step 902 may generate a de-identified copy of each data element as described above, and may generate the de-identified copy of the data collection by aggregating the de-identified copies of the data elements.

In some examples, Step 904 may comprise determining a confidence level that the de-identified copy generated by Step 902 does not include identified information. In some examples, a confidence level that the generated de-identified copy does not include identified information may be a numerical confidence level (such as a number in a particular range or group of numbers, a percent, a ratio, etc.), may be a discrete value (such as 'high', 'medium', 'low', etc.), and so forth. In some examples, determining a confidence level that the generated de-identified copy does not include identified information may comprise analyzing at least one of the data collection, the generated de-identified copy, or the process of generating the de-identified copy (that is, the process used by Step 902 to generate the de-identified copy). In one example, Step 904 may comprise analyzing the de-identified copy generated by Step 902 to determine the confidence level. In one example, Step 904 may comprise analyzing the data collection accessed by Step 902 to determine the confidence level. In one example, Step 904 may comprise analyzing the data collection accessed by Step 902 and the de-identified copy generated by Step 902 to determine the confidence level. In some examples, a machine learning model may be trained using training examples to determine confidence levels that de-identified copies of data collections does not include identified information, for example from the data collections and/or the de-identified copies. An example of such training example may include a sample data collection and/or a sample de-identified copy of the data collection, together with a label indicating a confidence level that the sample de-identified copy does not include identified information. Step 904 may use the trained machine learning model to analyze the data collection accessed by Step 902 and/or the de-identified copy generated by Step 902 and determine the confidence level that the de-identified copy generated by Step 902 does not include identified information. In some examples, the data collection accessed by Step 902 may include at least a first image and a second image, the de-identified copy of the data collection generated by Step 902 may include the second image but not the first image, and Step 904 may use method 920 to determining a confidence level that the de-identified copy generated by Step 902 does not include identified information.

In some examples, for each level of residual identified information of a plurality of levels of residual identified information, Step 904 may determine a likelihood that the de-identified copy of the data collection generated by Step 902 includes the level of residual identified information, for example as described below. Further, Step 904 may determine the confidence level that the generated de-identified copy does not include identified information based on the plurality of determined likelihoods. For example, the confidence level may be a multivariate function of the plurality of determined likelihoods. Some non-limiting examples of such multivariate function may include a linear multivariate function, a non-linear multivariate function, a polynomial multivariate function, an exponential multivariate function, a logarithmic multivariate function, a continuous multivariate function, a non-continuous multivariate function, and so forth. In another example, the plurality of determined likelihoods may represent a distribution, and the confidence level may be or may be based on a statistical parameter of the distribution, such as mean, median, mode, variance, standard deviation, skewness, location parameter, dispersion, scale parameter, shape parameter, and so forth. In some examples, a machine learning model may be trained using training examples to determine likelihoods that de-identified copies of data collections includes different levels of identified information. An example of such training example may include a sample de-identified copy of a sample data collection and a sample level of identified information, together with a label indicating the likelihood that the sample de-identified copy of the sample data includes the sample level of residual identified information. Step 904 may use the trained machine learning model to analyze the de-identified copy of the data collection and determine the likelihood that the de-identified copy of the data collection includes a level of residual identified information.

In some examples, for each particular type of identified information of a plurality of types of identified information, Step 904 may determine a likelihood that the de-identified copy of the data collection generated by Step 902 includes identified information of the particular type of identified information, for example as described below. Further, Step 904 may determine the confidence level that the de-identified copy generated by Step 902 does not include identified information based on the plurality of determined likelihoods. For example, the confidence level may be a multivariate function of the plurality of determined likelihoods. Some non-limiting examples of such multivariate function may include a linear multivariate function, a non-linear multivariate function, a polynomial multivariate function, an exponential multivariate function, a logarithmic multivariate function, a continuous multivariate function, a non-continuous multivariate function, and so forth. In another example, the plurality of determined likelihoods may represent a distribution, and the confidence level may be or may be based on a statistical parameter of the distribution, such as mean, median, mode, variance, standard deviation, skewness, location parameter, dispersion, scale parameter, shape parameter, and so forth. In some examples, a machine learning model may be trained using training examples to determine likelihoods that de-identified copies of the data collections includes identified information of the different types. An example of such training example may include a sample de-identified copy of a sample data collection and a sample type of identified information, together with a label indicating the likelihood that the sample de-identified copy of the sample data includes identified information of the sample type of identified information. Step 904 may use the trained machine learning model to analyze the de-identified copy of the data collection generated by Step 902 and determine the likelihood that the de-identified copy of the data collection generated by Step 902 includes identified information of a particular type of identified information.

In some examples, for each pair of a particular type of residual identified information and a level of residual identified information of a plurality of pairs, Step 904 may determine a likelihood that the de-identified copy of the data collection generated by Step 902 includes the level of residual identified information of the particular type of residual identified information, for example as described below. Further, Step 904 may determine the confidence level that the de-identified copy generated by Step 902 does not include identified information based on the plurality of determined likelihoods. For example, the confidence level may be a multivariate function of the plurality of determined likelihoods. Some non-limiting examples of such multivariate function may include a linear multivariate function, a non-linear multivariate function, a polynomial multivariate function, an exponential multivariate function, a logarithmic multivariate function, a continuous multivariate function, a non-continuous multivariate function, and so forth. In another example, the plurality of determined likelihoods may represent a distribution, and the confidence level may be or may be based on a statistical parameter of the distribution, such as mean, median, mode, variance, standard deviation, skewness, location parameter, dispersion, scale parameter, shape parameter, and so forth. In some examples, a machine learning model may be trained using training examples to determine likelihoods that de-identified copies of the data collections includes different levels of residual identified information of different types. An example of such training example may include a sample de-identified copy of a sample data collection, a sample type of identified information and a sample level of identified information, together with a label indicating the likelihood that the sample de-identified copy of the sample data includes the sample level of residual identified information of the sample type. Step 904 may use the trained machine learning model to analyze the de-identified copy of the data collection generated by Step 902 and determine the likelihood that the de-identified copy of the data collection generated by Step 902 includes the level of residual identified information of the particular type of residual identified information.

In some examples, the data collection accessed by Step 902 may be analyzed to determine a level of identified information in the data collection, for example as described herein. Further, Step 904 may determining the confidence level that the de-identified copy generated by Step 902 does not include identified information based on the determined level of identified information in the data collection. For example, when the determined level of identified information in the data collection is none or very low, the confidence level may be high. In another example, when the determined level of identified information in the data collection is high, the confidence level may vary based on other factors. In some examples, a machine learning model may be trained using training examples to determine levels of identified information in data collections. An example of such training example may include a sample data collection, together with a label indicating a level of identified information in the sample data collection. The trained machine learning model may be used to analyze the data collection accessed by Step 902 and determine the level of identified information in the data collection.

In some examples, Step 906 may comprise in response to a first value of the confidence level determined by Step 904, providing particular information based on the de-identified copy of the data collection to a first entity and to a second entity. Further, Step 908 may comprise, in response to a second value of the confidence level determined by Step 904, providing the particular information to the first entity and forgoing providing the particular information to the second entity. In one example, Step 908 may further comprise, in response to the second value of the confidence level, providing second particular information based on the de-identified copy of the data collection to the second entity, where the second particular information differs from the particular information. In one example, the particular information may be the de-identified copy of the data collection, may be a portion of the de-identified copy of the data collection, and so forth. In one example, the particular information may include a statistical measure of the de-identified copy of the data collection (such as mean, median, mode, variance, standard deviation, skewness, location parameter, dispersion, scale parameter, shape parameter, histogram, and so forth). In one example, providing information to an entity (for example, providing the particular information to the first entity by Step 906, providing the particular information to the second entity by Step 906, providing the particular information to the first entity by Step 908, providing the second particular information to the second entity by Step 908, etc.) may comprise storing the information in memory (for example, in memory unit 210, in shared memory module 410, in memory 700, etc.), for example at a specific location in the memory that enables another process or device to access the information. In one example, providing information to an entity (for example, providing the particular information to the first entity by Step 906, providing the particular information to the second entity by Step 906, providing the particular information to the first entity by Step 908, providing the second particular information to the second entity by Step 908, etc.) may comprise at least one of providing the information to an external device (for example, to computerized data analysis device 144, to a computing device such as computing device 200, to cloud platform 400, etc.), providing the information to a user (for example, through a user interface, visually, audibly, textually, numerically, graphically, etc.), or providing the information over a communication network (for example over communication network 130, using communication module 230, using internal communication module 440, using external communication module 450, etc.).

In some examples, in response to the first value of the confidence level, specific information based on the de-identified copy of the data collection may be provided to the first entity and to the second entity. The specific information differs from the particular information. Further, in some examples, in response to the second value of the confidence level, the specific information may be provided to the second entity, and providing the specific information to the first entity may be forwent. The specific information may be provided as described above in relation to the particular information.

In some examples, the data collection accessed by Step 902 may include at least a first image and a second image, and the de-identified copy of the data collection generated by Step 902 may include the second image but not the first image. In this example, Step 922 may comprise analyzing the first image to determine a visual characteristic, Step 924 may comprise analyzing the second image to determine a likelihood that the second image includes the visual characteristic, and Step 926 may comprise determining the confidence level that the generated de-identified copy does not include identified information based on the determined likelihood. In one example, the visual characteristic may be associated with a face of an individual, such as a distance between two face features of the face, a size of a face feature of the face, a shape of a face feature of the face, a color of at least part of the face, a texture of at least part of the face, and so forth. In another example, the visual characteristic may be associated with an article of clothing, such as a color of at least part of the article of clothing, a pattern on the article of clothing, a shape of the article of clothing, and so forth. In yet another example, the visual characteristic may be associated with a skin marking, such as a shape, color, pattern, size, and so forth.

In some examples, Step 922 may comprise analyzing the first image to determine a visual characteristic. In one example, a convolution of at least part of the first image may be calculated to obtain a result value of the calculated convolution, and Step 922 may determine the visual characteristic based on the result value. For example, in response to one result value of the calculated convolution, Step 922 may determine one visual characteristic, and in response to another result value of the calculated convolution, Step 922 may determine another visual characteristic. In one example, a machine learning model may be trained using training examples to identify visual characteristics from images. An example of such training example may include a sample image, together with a label indicating a visual characteristic associated with the sample image. Step 922 may use the trained machine learning model to analyze the first image and determine the visual characteristic.

In some examples, Step 924 may comprise analyzing the second image to determine a likelihood that the second image includes the visual characteristic determined by Step 922. In one example, a convolution of at least part of the second image may be calculated to obtain a result value of the calculated convolution, and Step 924 may determine the likelihood that the second image includes the visual characteristic based on the result value. For example, in response to a first result value of the calculated convolution, Step 924 may determine a likelihood that is above a selected threshold that the second image includes the visual characteristic, and in response to a second result value of the calculated convolution, Step 924 may determine that there is no likelihood above the selected threshold that the second image includes the visual characteristic. In one example, a machine learning model may be trained using training examples to determine that images includes specific visual characteristics. An example of such training example may include a sample image and an indication of a sample visual characteristic, together with a label indicating whether the sample image includes the sample visual characteristic. Step 924 may use the trained machine learning model to analyze the second image and determine a likelihood that the second image includes the visual characteristic determined by Step 922.

In some examples, Step 926 may comprise determining the confidence level that the de-identified copy generated by Step 902 does not include identified information based on the likelihood determined by Step 924. For example, in response to a first likelihood determined by Step 924, Step 926 may determine one confidence level that the de-identified copy generated by Step 902 does not include identified information, and in response to a second likelihood determined by Step 924, Step 926 may determine another confidence level that the de-identified copy generated by Step 902 does not include identified information. In another example, the confidence level that the de-identified copy generated by Step 902 does not include identified information may be a function of the likelihood determined by Step 924. Some non-limiting examples of such function may include a linear function, a non-linear function, a polynomial function, an exponential function, a logarithmic function, a continuous function, a non-continuous function, and so forth.

In some examples, for example in response to the second value of the confidence level, method 900 may further comprise initiating an action to generate a second de-identified copy of the data collection accessed by Step 902 (the second de-identified copy may differ from the de-identified copy), and providing specific information based on the second de-identified copy of the data collection to the second entity. For example, initiating the action may include at least one of performing the action, or causing another process or another device to perform the action (for example by providing a signal to the other process of the other device configure to cause the other process of the other device to perform the action). In one example, the second de-identified copy of the data collection accessed by Step 902 may be generated as described above in relation to Step 902. Further, specific information may be provided as described above in relation to the particular information. In some examples, the action to generate the second de-identified copy of the data collection may comprise presenting to a user at least part of the de-identified copy of the data collection generated by Step 902, receiving from the user a response to the presentation, and generating the second de-identified copy of the data collection based on the received response. In one example, the at least part of the de-identified copy of the data collection may be presented to the user visually, textually, graphically, numerically, audibly, through a user interface, and so forth. In one example, the response to the presentation may be received from the user through the user interface, through voice commands, through gestures, through an input device, and so forth. In one example, in response to a first received response, one version of the second de-identified copy of the data collection may be generated, and in response to a second received response, another version of the second de-identified copy of the data collection may be generated. In one example, the received response may include modifications to the de-identified copy of the data collection generated by Step 902 (for example, a reduction of a part of the de-identified copy of the data collection generated by Step 902, a change of at least one value in the de-identified copy of the data collection generated by Step 902, etc.), and the second de-identified copy of the data collection may include the modifications.

FIG. 10 illustrates an example of a method 1000 for estimating residual privacy loss after data de-identification. In this example, method 1000 may comprise: accessing a data collection to generate a de-identified copy of the data collection (Step 902); determining a first amount of residual identified information of a first type of residual identified information in the generated de-identified copy (Step 1004); determining a first amount of residual identified information of a first type of residual identified information in the generated de-identified copy (Step 1006); selecting a usage policy for the generated de-identified copy based on the first amount of residual identified information and the second amount of residual identified information in the generated de-identified copy (Step 1008); and implementing the selected usage policy (Step 1010). In some implementations, method 1000 may comprise one or more additional steps, while some of the steps listed above may be modified or excluded. In some implementations, one or more steps illustrated in FIG. 10 may be executed in a different order and/or one or more groups of steps may be executed simultaneously and/or a plurality of steps may be combined into single step and/or a single step may be broken down to a plurality of steps.

In some examples, Step 1004 may comprise determining a first amount of residual identified information of a first type of residual identified information in the de-identified copy generated by Step 902. In some examples, Step 1006 may comprise determining a second amount of residual identified information of a second type of residual identified information in the de-identified copy generated by Step 902.

The second type may differ from the first type. Some non-limiting examples of types of residual identified information may include residual identified information associated with visual data, residual identified information associated with audio data, residual identified information associated with textual data, residual identified information associated with numerical data, residual identified information associated with temporal data, residual identified information likely to identify particular individuals, residual identified information likely to identify groups that particular individuals belong to, residual identified information likely to identify small groups that particular individuals belong to, residual identified information likely to identify larger groups that particular individuals belong to, and so forth. In some examples, the first type of residual identified information (and/or the second type of residual identified information) may be at least one of residual identified information associated with visual data, residual identified information associated with audio data, residual identified information associated with textual data, residual identified information associated with numerical data, or residual identified information associated with temporal data. In some examples, the first type of residual identified information may be associated with visual data and the second type of residual identified information may be associated with audio data. In some examples, the first type of residual identified information may be associated with visual data and the second type of residual identified information may be associated with textual data. In some examples, the first type of residual identified information may be associated with visual data and the second type of residual identified information may be associated with numerical data. In some examples, the first type of residual identified information may be associated with visual data and the second type of residual identified information may be associated with temporal data. In some examples, the first type of residual identified information may be associated with numerical data and the second type of residual identified information may be associated with textual data. In some examples, the first type of residual identified information may be information likely to identify particular individuals and the second type of residual identified information may be information likely to identify groups that particular individuals belong to. In some examples, the first type of residual identified information may be information likely to identify small groups that particular individuals belong to, and the second type of residual identified information may be information likely to identify larger groups that particular individuals belong to.

In some examples, residual identified information associated with visual data may include one or more images and/or one or more videos that include identified information, such as faces, identifiable skin features, depiction of identifiable textual data, unique body structure, and so forth. In one example, the one or more images and/or one or more videos may be analyzed (for example using Step 1004 and/or Step 1006) to determine an amount of residual identified information in the images and/or videos. For example, the images and/or videos may be analyzed using face detection algorithm to detect faces, may be analyzed using OCR and/or Natural Language Processing (NLP) algorithms to detect depictions of identifiable textual data, using an image classification algorithm to classify the images and/or videos to a class corresponding to 'including identifiable information' or to a class corresponding to 'not including identifiable information', and so forth. In some examples, residual identified information associated with audio data may include one or more audio recordings that include voices and/or audible presentation of identifiable information (such as names, addresses, etc.). In one example, the audio recordings may be analyzed (for example using Step 1004 and/or Step 1006) to determine an amount of residual identified information in the audio recordings. For example, the audio recordings may be analyzed using speaker recognition algorithm to detect identifiable speakers, may be analyzed using speech recognition and/or NLP algorithms to detect audible presentations of identifiable information, using an audio classification algorithm to classify the audio recordings to a class corresponding to 'including identifiable information' or to a class corresponding to 'not including identifiable information', and so forth. In some examples, residual identified information associated with textual data may include names, addresses, and so forth. In one example, textual information (such as free text, document, textual form, etc.) may be analyzed (for example using Step 1004 and/or Step 1006) to determine an amount of residual identified information in the textual information. For example, the textual information may be analyzed using NLP algorithms to detect identifiable information. In some examples, residual identified information associated with numerical data may include identification numbers, zip codes, dates of birth, and so forth. In one example, numerical information (such as a number, a stream of numbers or a collection of numbers) may be analyzed (for example using Step 1004 and/or Step 1006) to determine an amount of residual identified information in the numerical information. For example, the numerical information may be analyzed using a classification algorithm to classify the numerical information to a class corresponding to 'including identifiable information' or to a class corresponding to 'not including identifiable information'. In some examples, residual identified information associated with temporal data may include identifiable dates and/or numbers, such as a date of birth, a date and time of an appointment, and so forth. In one example, temporal information (such as dates, time, etc.) may be analyzed (for example using Step 1004 and/or Step 1006) to determine an amount of residual identified information in the temporal information. For example, the temporal information may be analyzed using a classification algorithm to classify the temporal information to a class corresponding to 'including identifiable information' or to a class corresponding to 'not including identifiable information'. Some non-limiting examples of residual identified information likely to identify particular individuals may include names, identification numbers, addresses, face images, time of appointment, and so forth. Some non-limiting examples of residual identified information likely to identify groups that particular individuals belong to may include zip code, date of birth, address of a communal living facility, name of school, and so forth. In some examples, residual identified information likely to identify small groups that particular individuals belong to may include residual identified information likely to identify groups smaller than a selected threshold, and residual identified information likely to identify larger groups that particular individuals belong to may include residual identified information likely to identify groups larger than the selected threshold.

In some examples, determining an amount of residual identified information of a particular type of residual identified information in the de-identified copy generated by Step 902 (for example, determining by Step 1004 the first amount of residual identified information of a first type of residual identified information in the de-identified copy generated by Step 902, determining by Step 1006 a second amount of residual identified information of a second type of residual identified information in the de-identified copy generated by Step 902, etc.) may comprise analyzing at least one of the data collection accessed by Step 902 or the de-identified copy generated by Step 902 to determine the amount of residual identified information of a particular type of residual identified information in the de-identified copy generated by Step 902. In one example, the de-identified copy generated by Step 902 may be analyzed to determine the first and/or second amounts of residual identified information in the generated de-identified copy by Step 1004 and/or Step 1006. In one example, the data collection accessed by Step 902 may be analyzed to determine the first and second amounts of residual identified information in the generated de-identified copy by Step 1004 and/or Step 1006. In one example, the de-identified copy generated by Step 902 and the data collection accessed by Step 902 may be analyzed to determine the first and second amounts of residual identified information in the generated de-identified copy by Step 1004 and/or Step 1006. In one example, a machine learning model may be trained using training examples to determine amounts of residual identified information of different types of residual identified information in data elements. An example of such training examples may include a sample data element and a sample type of residual identified information, together with a label indicating the amount of the residual identified information of the sample type of residual identified information in the sample data element. In one example, Step 1004 may use the trained machine learning model to analyze the data collection accessed by Step 902 and/or the de-identified copy generated by Step 902 to determine the first amount of residual identified information of the first type of residual identified information in the de-identified copy generated by Step 902. In another example, Step 1006 may use the trained machine learning model to analyze the data collection accessed by Step 902 and/or the de-identified copy generated by Step 902 to determine the second amount of residual identified information of the second type of residual identified information in the de-identified copy generated by Step 902. In some examples, instances of identified information may be counted in the de-identified copy generated by Step 902 to determine the amount of residual identified information of the particular type of residual identified information in the de-identified copy generated by Step 902. In some examples, instances of suspected identified information may be detected in the de-identified copy generated by Step 902, each instance may be assigned with a likelihood that the instance of suspected identified information is indeed an identified information, and a function (such as a sum, a sum of squares, etc.) of the likelihoods may be calculated to thereby determine the amount of residual identified information of the particular type of residual identified information in the de-identified copy generated by Step 902.

In some examples, the first type of residual identified information of Step 1004 may be associated with visual data, for example as described above. In one example, Step 1004 may calculate a convolution of at least part of an image included in the de-identified copy of the data collection generated by Step 902 to obtain a result value of the calculated convolution, for example as described above. Further, Step 1004 may determine the first amount of residual identified information based on the result value of the calculated convolution. For example, in response to one result value, Step 1004 may determine one first amount of residual identified information, and in response to another result value, Step 1004 may determine another first amount of residual identified information.

In some examples, the first type of residual identified information of Step 1004 may be associated with visual data, for example as described above. In one example, Step 1004 may calculate a first convolution of at least part of an image included in the data collection accessed by Step 902 to obtain a result value of the first calculated convolution, and may calculate a second convolution of at least part of an image included in the de-identified copy of the data collection generated by Step 902 to obtain a result value of the second calculated convolution. Further, Step 1004 may determine the first amount of residual identified information based on the result value of the first calculated convolution and the result value of the second calculated convolution. For example, in response to one pair of result value of the first calculated convolution and result value of the second calculated convolution, Step 1004 may determine one first amount of residual identified information, and in response to another pair of result value of the first calculated convolution and result value of the second calculated convolution, Step 1004 may determine another first amount of residual identified information. In another example, Step 1004 may calculate a function of the result value of the first calculated convolution and the result value of the second calculated convolution, thereby determining the first amount of residual identified information. Some non-limiting examples of such function may include a linear function, a non-linear function, a polynomial function, an exponential function, a logarithmic function, a continuous function, a non-continuous function, and so forth.

In some examples, the first type of residual identified information of Step 1004 may be associated with audio data, for example as described above. In one example, Step 1004 may calculate a convolution of at least part of audio data included in the de-identified copy of the data collection generated by Step 902 to obtain a result value of the calculated convolution, for example as described above. Further, Step 1004 may determine the first amount of residual identified information based on the result value of the calculated convolution. For example, in response to one result value, Step 1004 may determine one first amount of residual identified information, and in response to another result value, Step 1004 may determine another first amount of residual identified information.

In some examples, the first type of residual identified information of Step 1004 may be associated with audio data, for example as described above. In one example, Step 1004 may calculate a first convolution of at least part of audio data included in the data collection accessed by Step 902 to obtain a result value of the first calculated convolution, and may calculate a second convolution of at least part of audio data included in the de-identified copy of the data collection generated by Step 902 to obtain a result value of the second calculated convolution. Further, Step 1004 may determine the first amount of residual identified information based on the result value of the first calculated convolution and the result value of the second calculated convolution. For example, in response to one pair of result value of the first calculated convolution and result value of the second calculated convolution, Step 1004 may determine one first amount of residual identified information, and in response to another pair of result value of the first calculated convolution and result value of the second calculated convolution, Step 1004 may determine another first amount of residual identified information. In another example, Step 1004 may calculate a function of the result value of the first calculated convolution and the result value of the second calculated convolution, thereby determining the first amount of residual identified information. Some non-limiting examples of such function may include a linear function, a non-linear function, a polynomial function, an exponential function, a logarithmic function, a continuous function, a non-continuous function, and so forth.

In some examples, the data collection accessed by Step 902 may be analyzed to identify a particular piece of information in the data collection and to determine a context of the particular piece of information in the data collection. Further, the de-identified copy of the data collection generated by Step 902 may be analyzed to detect the particular piece of information and to determine a context of the detected particular piece of information in the de-identified copy of the data collection. Further, Step 1004 may determine the first amount of residual identified information based on the determined context of the particular piece of information in the data collection and the determined context of the detected particular piece of information in the de-identified copy of the data collection. For example, when the two contexts are identical or have high affinity to each other, the determined first amount may be higher compared to when the two contexts are different of have low affinity to each other. For example, the particular piece of information may be the word 'May', which may be a first name of a person or a name of a month. When the contexts of the word 'May' are different (for example, one is a first name and the other is a name of a month based on words appearing next to the word 'May'), the first amount may be lower than when the contexts of the word 'May' are identical (for example, both are first name of a person based on words appearing next to the word 'May').

In some examples, the first type of residual identified information of Step 1004 may be associated with temporal data. Further, the data collection accessed by Step 902 may be analyzed to identify a particular date in the data collection and to determine a context of the particular date in the data collection. Further, the de-identified copy of the data collection generated by Step 902 may be analyzed to detect the particular date and to determine a context of the detected particular date in the de-identified copy of the data collection. Further, Step 1004 may determine the first amount of residual identified information based on the determined context of the particular date in the data collection and the determined context of the detected particular date in the de-identified copy of the data collection. For example, when the two contexts are identical or have high affinity to each other, the determined first amount may be higher compared to when the two contexts are different of have low affinity to each other. In another example, when the determined context of the particular date in the data collection is 'appointment time' (for example, based on the location of the date in a form or in a digital memory), and the determined context of the detected particular date in the de-identified copy of the data collection is 'unknown', the determined first amount may be higher compared to when any one of the determined contexts is 'national holiday' (for example, based on the location of the date in a form or in a digital memory).

In some examples, Step 1008 may comprise selecting a usage policy for the de-identified copy generated by Step 902 based on the first amount of residual identified information in the generated de-identified copy determined by Step 1004 and the second amount of residual identified information in the generated de-identified copy determined by Step 1006. In one example, in response to one pair of values of the first amount and the second amount, Step 1008 may select a first usage policy, and in response to another pair of values of the first amount and the second amount, Step 1008 may select a second usage policy, the second usage policy may differ from the first usage policy. In some examples, a data-structure (such as a map, a table in a database, etc.) may associate pairs of amounts with different usage policies, and Step 1008 may access the data-structure using the first amount of residual identified information in the generated de-identified copy determined by Step 1004 and the second amount of residual identified information in the generated de-identified copy determined by Step 1006 to select the usage policy for the de-identified copy generated by Step 902. In some examples, a function of the first amount of residual identified information and the second amount of residual identified information may be calculated to thereby obtain a result value, and Step 1008 may select the usage policy for the generated de-identified copy based on the result value. In some examples, a function of the first amount of residual identified information and the second amount of residual identified information may be calculated to thereby obtain a risk level, and Step 1008 may select the usage policy for the generated de-identified copy based on the risk level. Some non-limiting examples of such function may include a linear function, a non-linear function, a polynomial function, an exponential function, a logarithmic function, a continuous function, a non-continuous function, and so forth. In one example, the function may be a non-linear function. Some non-limiting examples of usage policies may include private usage only of the de-identified copy generated by Step 902, access to the de-identified copy generated by Step 902 limited to a selected group of entities, public access to the de-identified copy generated by Step 902, access to the de-identified copy generated by Step 902 requires manual review of an authorized person, access to the de-identified copy generated by Step 902 is limited to particular parts of the de-identified copy generated by Step 902, and so forth.

In some examples, Step 1010 may comprise implementing the usage policy selected by Step 1008. For example, implementing the usage policy may include enforcing access restrictions to the de-identified copy generated by Step 902 based on the selected usage policy. In another example, implementing the usage policy may include providing information to another process or another device indicating the selected usage policy. For example, the other process or other device may be configured to implement the selected usage policy in response to the provided information. In one example, providing the information may comprise storing the information in memory (for example, in memory unit 210, in shared memory module 410, in memory 700, etc.), for example at a specific location in the memory that enables the other process or device to access the information. In another example, providing the information may comprise at least one of providing the information to an external device (for example, to computerized data analysis device 144, to a computing device such as computing device 200, to cloud platform 400, etc.), providing the information to a user (for example, through a user interface, visually, audibly, textually, numerically, graphically, etc.), or providing the information over a communication network (for example over communication network 130, using communication module 230, using internal communication module 440, using external communication module 450, etc.).

It will also be understood that the system according to the invention may be a suitably programmed computer, the computer including at least a processing unit and a memory unit. For example, the computer program can be loaded onto the memory unit and can be executed by the processing unit. Likewise, the invention contemplates a software program being readable by a computer for executing the method of the invention. The invention further contemplates a non-transitory computer readable medium storing a software program comprising data and/or computer implementable instruction for currying out any one or more of the methods described above.

What is claimed is:

1. A non-transitory computer readable medium storing a software program comprising data and computer implementable instructions for carrying out a method for assigning confidence to data de-identification, the method comprising:
   accessing a data collection to generate a de-identified copy of the data collection;
   determining a confidence level that the generated de-identified copy does not include identified information;
   in response to a first value of the confidence level, providing particular information based on the de-identified copy of the data collection to a first entity and to a second entity; and
   in response to a second value of the confidence level, providing the particular information to the first entity and forgoing providing the particular information to the second entity.

2. The non-transitory computer readable medium of claim 1, wherein the method further comprises analyzing the generated de-identified copy to determine the confidence level.

3. The non-transitory computer readable medium of claim 1, wherein the method further comprises analyzing the data collection to determine the confidence level.

4. The non-transitory computer readable medium of claim 1, wherein the method further comprises analyzing the data collection and the generated de-identified copy to determine the confidence level.

5. The non-transitory computer readable medium of claim 1, wherein the method further comprises:
   for each level of residual identified information of a plurality of levels of residual identified information, determining a likelihood that the de-identified copy of the data collection includes the level of residual identified information; and
   determining the confidence level that the generated de-identified copy does not include identified information based on the plurality of determined likelihoods.

6. The non-transitory computer readable medium of claim 1, wherein the method further comprises:
   for each particular type of identified information of a plurality of types of identified information, determining a likelihood that the de-identified copy of the data collection includes identified information of the particular type of identified information; and
   determining the confidence level that the generated de-identified copy does not include identified information based on the plurality of determined likelihoods.

7. The non-transitory computer readable medium of claim 1, wherein the method further comprises:
   for each pair of a particular type of residual identified information and a level of residual identified information of a plurality of pairs, determining a likelihood that the de-identified copy of the data collection includes the level of residual identified information of the particular type of residual identified information; and
   determining the confidence level that the generated de-identified copy does not include identified information based on the plurality of determined likelihoods.

8. The non-transitory computer readable medium of claim 1, wherein the method further comprises:
   analyzing the data collection to determine a level of identified information in the data collection; and
   determining the confidence level that the generated de-identified copy does not include identified information based on the determined level of identified information in the data collection.

9. The non-transitory computer readable medium of claim 1, wherein the data collection includes at least a first image and a second image, the de-identified copy of the data collection includes the second image and does not include the first image, and the method further comprises:
   analyzing the first image to determine a visual characteristic;
   analyzing the second image to determine a likelihood that the second image includes the visual characteristic; and
   determining the confidence level that the generated de-identified copy does not include identified information based on the determined likelihood.

10. The non-transitory computer readable medium of claim 9, wherein the visual characteristic is associated with a face of an individual.

11. The non-transitory computer readable medium of claim 9, wherein the method further comprises:
    calculating a convolution of at least part of the first image to obtain a result value of the calculated convolution; and
    determining the visual characteristic based on the result value.

12. The non-transitory computer readable medium of claim 9, wherein the method further comprises:
    calculating a convolution of at least part of the second image to obtain a result value of the calculated convolution; and
    determining the likelihood that the second image includes the visual characteristic based on the result value.

13. The non-transitory computer readable medium of claim 1, wherein the method further comprises, in response to the second value of the confidence level, providing second particular information based on the de-identified copy of the data collection to the second entity, the second particular information differs from the particular information.

14. The non-transitory computer readable medium of claim 1, wherein the particular information is the de-identified copy of the data collection.

15. The non-transitory computer readable medium of claim 1, wherein the particular information includes a statistical measure of the de-identified copy of the data collection.

16. The non-transitory computer readable medium of claim 1, wherein the method further comprises, after providing the particular information:
    in response to the first value of the confidence level, providing specific information based on the de-identified copy of the data collection to the first entity and to the second entity, the specific information differs from the particular information; and
    in response to the second value of the confidence level, providing the specific information to the second entity and forgoing providing the specific information to the first entity.

17. The non-transitory computer readable medium of claim 1, wherein the method further comprises, in response to the second value of the confidence level:
- initiating an action to generate a second de-identified copy of the data collection, the second de-identified copy differs from the de-identified copy; and
- providing specific information based on the second de-identified copy of the data collection to the second entity.

18. The non-transitory computer readable medium of claim 17, wherein the action to generate the second de-identified copy of the data collection comprises:
- presenting to a user at least part of the de-identified copy of the data collection;
- receiving from the user a response to the presentation; and
- generating the second de-identified copy of the data collection based on the received response.

19. A system for assigning confidence to data de-identification, the system comprising:
- at least one processing unit configured to:
  - accessing a data collection to generate a de-identified copy of the data collection;
  - determining a confidence level that the generated de-identified copy does not include identified information;
  - in response to a first value of the confidence level, providing particular information based on the de-identified copy of the data collection to a first entity and to a second entity; and
  - in response to a second value of the confidence level, providing the particular information to the first entity and forgoing providing the particular information to the second entity.

20. A method for assigning confidence to data de-identification, the method comprising:
- accessing a data collection to generate a de-identified copy of the data collection;
- determining a confidence level that the generated de-identified copy does not include identified information;
- in response to a first value of the confidence level, providing particular information based on the de-identified copy of the data collection to a first entity and to a second entity; and
- in response to a second value of the confidence level, providing the particular information to the first entity and forgoing providing the particular information to the second entity.

\* \* \* \* \*